United States Patent
Saji et al.

(10) Patent No.: US 10,561,749 B2
(45) Date of Patent: Feb. 18, 2020

(54) NUCLEAR MEDICINE DIAGNOSTIC IMAGING AGENT

(71) Applicants: Kyoto University, Kyoto (JP); ARKRAY, Inc., Kyoto (JP)

(72) Inventors: Hideo Saji, Kyoto (JP); Hiroyuki Kimura, Kyoto (JP); Anna Miyazaki, Kyoto (JP); Hirokazu Matsuda, Kyoto (JP); Shuichi Nakanishi, Kyoto (JP)

(73) Assignees: Kyoto University, Kyoto (JP); ARKRAY, Inc., Kyoto (JP)

( * ) Notice: Subject to any disclaimer, the term of this patent is extended or adjusted under 35 U.S.C. 154(b) by 614 days.

(21) Appl. No.: 15/200,346

(22) Filed: Jul. 1, 2016

(65) Prior Publication Data
US 2017/0000913 A1   Jan. 5, 2017

(30) Foreign Application Priority Data

Jul. 3, 2015 (JP) ................. 2015-134792
Jun. 30, 2016 (JP) ................. 2016-130823

(51) Int. Cl.
*A61K 51/04* (2006.01)
*A61K 49/00* (2006.01)
*C07D 495/14* (2006.01)

(52) U.S. Cl.
CPC ...... *A61K 51/0459* (2013.01); *A61K 49/0004* (2013.01); *A61K 51/0431* (2013.01); *C07D 495/14* (2013.01)

(58) Field of Classification Search
CPC ................. A61K 49/00; A61K 51/00
See application file for complete search history.

(56) References Cited

U.S. PATENT DOCUMENTS

2010/0120805 A1   5/2010 Hsieh et al.
2014/0120036 A1*  5/2014 Black ............... C07B 59/00
                                                    424/1.89

FOREIGN PATENT DOCUMENTS

| WO | 2007/109279 | A2 | 9/2007 | |
|----|-------------|----|--------|---|
| WO | 2007/109279 | A3 | 9/2007 | |
| WO | 2009/033581 | A1 | 3/2009 | |
| WO | WO-2009033581 | A1 * | 3/2009 | ......... C07D 491/147 |

OTHER PUBLICATIONS

Emily B. Corcoran et al., Imaging EGFR and HER2 by PET and SPECT: A Review, Medicinal Research Reviews, 34, 596-643. (Year: 2014).*
Pal et al., "Radiosynthesis and Initial in Vitro Evaluation of [18F]F-PEG6-IPQA—A Novel PET Radiotracer for Imaging EGFR Expression-Activity in Lung Carcinomas," Molecular Imaging and Biology, 13: 853-861 (2011).

Extended European Search Report issued in corresponding European Patent Application No. 16177639.8 dated Nov. 18, 2016.
Yeh et al., "Molecular imaging of active mutant L858R EGF receptor (EGFR) kinase-expressing nonsmall cell lung carcinomas using PET/CT," PNAS, 108: 1603-1608 (2011).
Pantaleo et al., "Experimental results and related clinical implications of PET detection of epidermal growth factor receptor (EGFr) in cancer," Annals of Oncology, 20: 213-226 (2009).
Corcoran et al., "Imaging EGFR and HER2 by PET and SPECT: A Review," Medicinal Research Reviews, 34: 596-643 (2014).
Wu et al., "Design and Synthesis of Tetrahydropyridothieno[2,3-d]pyrimidine Scaffold Based Epidermal Growth Factor Receptor (EGFR) Kinase Inhibitors: The Role of Side Chain Chirality and Michael Acceptor Group for Maximal Potency," Journal of Medicinal Chemistry, 53: 7316-7326 (2010).
Abourbeh et al., "Identifying erlotinib-sensitive non-small cell lung carcinoma tumors in mice using [11C]erlotinib PET," EJNMMI Research, 5: 4 (2015).
Slobbe et al., "Development of [18F]afatinib as new TKI-PET tracer for EGFR positive tumors," Nuclear Medicine and Biology, 41: 749-757 (2014).

* cited by examiner

*Primary Examiner* — Johann R Richter
*Assistant Examiner* — Jagadishwar R Samala
(74) *Attorney, Agent, or Firm* — Morgan, Lewis & Bockius LLP

(57) ABSTRACT

Provided is a radioactive labeled compound capable of detecting a secondary mutation of an epidermal growth factor receptor, where the compound is represented by Formula (1) or a pharmaceutically acceptable salt thereof, where $R_1$, $R_2$, and Y are as defined.

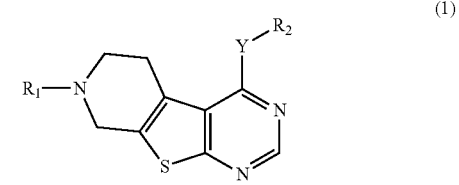

(1)

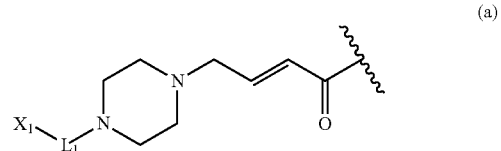

(a)

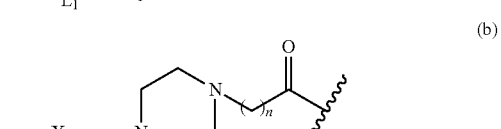

(b)

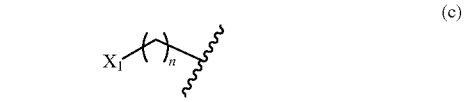

(c)

12 Claims, 1 Drawing Sheet

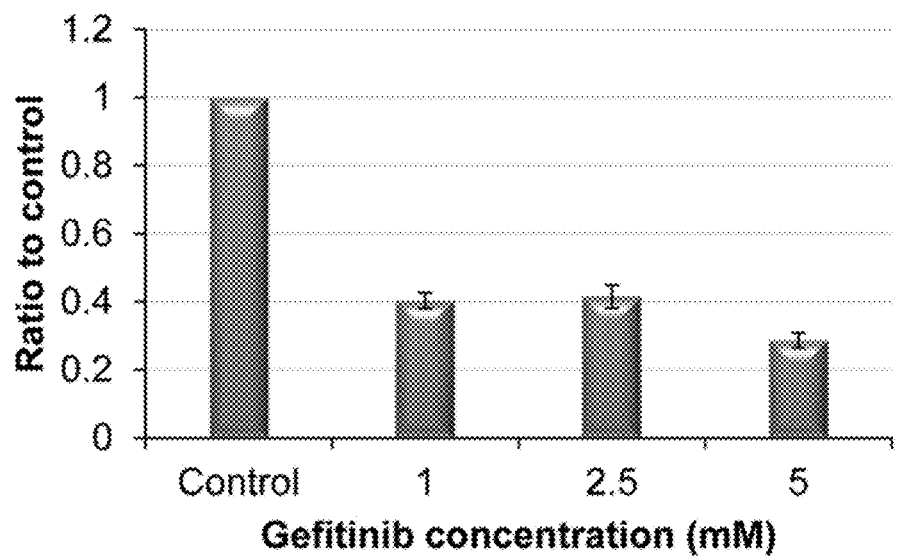
FIG.1
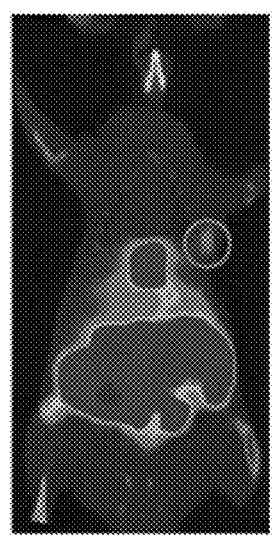 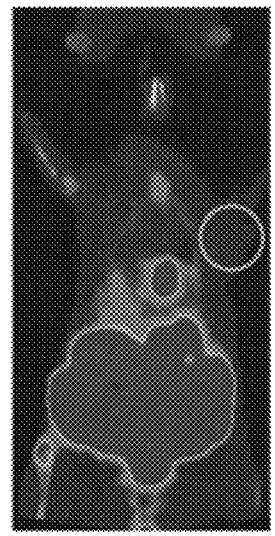
FIG.2A  FIG.2B

NUCLEAR MEDICINE DIAGNOSTIC IMAGING AGENT

BACKGROUND OF THE INVENTION

1. Field of the Invention

The present disclosure relates to a radioactive labeled compound with a tetrahydropyridothieno[2,3-d]pyrimidine skeleton that can in one aspect provide information for detecting a secondary mutation of an epidermal growth factor receptor (EGFR).

2. Description of Related Art

Lung cancer, which is the number one worldwide cause of death due to cancer, is roughly divided into small cell lung cancer and non-small cell lung cancer according to the histological type thereof. It is known that the EGFR gene that codes for EGFR, which is a transmembrane tyrosine kinase receptor, has mutated in 10% to 30% of patients with non-small cell lung cancer which accounts for 80% of lung cancer. The EGFR is activated when mutated and this activation is considered to play a role in cancer growth, etc. Furthermore, once the mutation of the EGFR gene was found, an EGFR-TKI (an epidermal growth factor receptor tyrosine kinase inhibitor), which is a molecular target drug, was considered to be more effective than common anticancer agents. In recent years, therefore, when a patient is diagnosed as having lung cancer, the possible presence of a mutation in the genes of the patient is checked by a genetic test (for example, Hsin Hsien Yeh et al., PNAS, Jan. 25, 2011; vol. 108, no. 4, 1603-1608). These genetic tests are often carried out using cancer tissue collected by biopsy. However, an invasive biopsy on a cancer patient has various risks associated with it and also results in a heavy physical burden. Therefore, there has been a need for new methods that provide alternatives to conventional genetic tests and that avoid various risks associated with the biopsy. As one of the methods, radioactive imaging probes for nuclear medicine diagnosis that can detect EGFR in cancer have been studied (for example, M. A. Pantaleo et al., Annals of Oncology 2009, 20: 213-226; and Emily B. Corcoran et al., Medicinal Research Reviews 2014, 34: 596-643).

Despite the success of the EGFR-TKI, resistance develops within a year and as a result, the EGFR-TKI may no longer provide sufficient therapeutic effects. Since a secondary mutation is considered to play a role in approximately half the cases that develop resistance, it becomes necessary to conduct the genetic test again after the start of treatment with the EGFR-TKI.

SUMMARY OF THE INVENTION

As described above, imaging probes for detecting the EGFR have been studied but a method capable of noninvasively detecting a secondary mutation of the EGFR has not yet been developed. The present disclosure meets this need by providing a radioactive labeled compound capable of detecting a secondary mutation of the EGFR.

In one aspect, the present disclosure relates to a nuclear medicine diagnostic imaging agent, including a compound represented by Formula (1) or a pharmaceutically acceptable salt thereof.

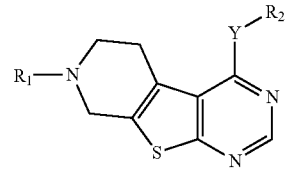

In Formula (1),
$R_1$ is a group represented by Formula (a), (b) or (c):

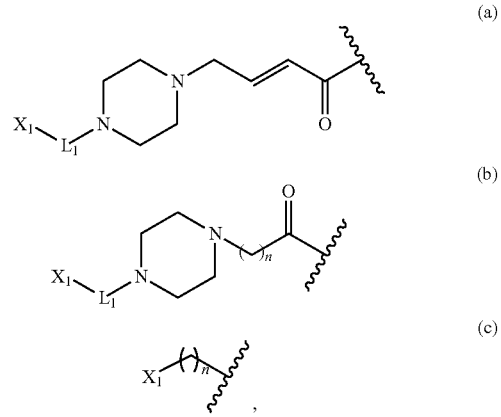

$R_2$ is a group represented by Formula (d) or (e):

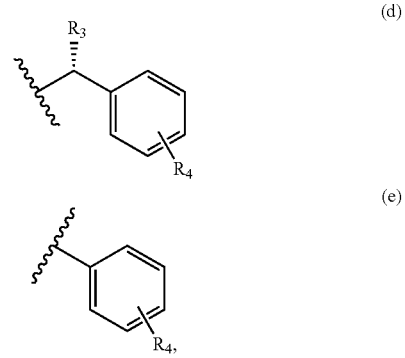

and
Y is —NH— or —O—,
wherein,
in Formulae (a) and (b), $L_1$ is a bond, an alkanediyl group having 1 to 10 carbon atoms, or

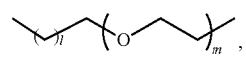

wherein 1 is 0 to 5, and m is the number of repeating ethyleneoxy groups (—$OC_2H_4$—) and is 1 to 5,
in Formulae (b) and (c), n is an integer of 1 to 3,
in Formulae (a), (b) and (c), $X_1$ is a radioactive halogen atom or —[$^{11}$C]$CH_3$,
in Formula (d), $R_3$ is an alkyl group having 1 to 4 carbon atoms that may be substituted with halogen, a hydroxyalkyl group having 1 to 4 carbon atoms, or an alkoxyalkyl group having 1 to 4 carbon atoms, and in Formulae (d) and (e), $R_4$ is a hydrogen atom or a halogen atom.

In one aspect, the present disclosure relates to a compound represented by Formula (1) or a pharmaceutically acceptable salt thereof.

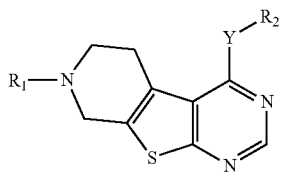
(1)

In Formula (1),
$R_1$ is a group represented by Formula (a), (b) or (c):

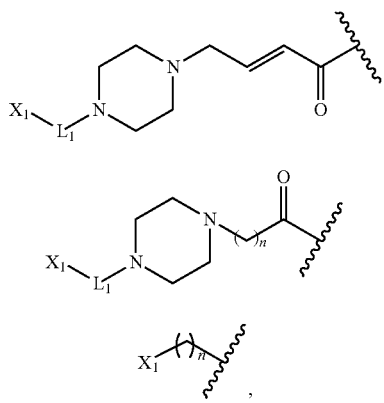

$R_2$ is a group represented by Formula (d) or (e):

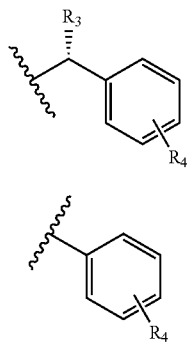

and
Y is —NH— or —O—,
wherein,
in Formulae (a) and (b), $L_1$ is a bond, an alkanediyl group having 1 to 10 carbon atoms, or

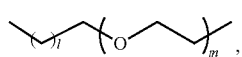

wherein l is 0 to 5, and m is the number of repeating ethyleneoxy groups (—$OC_2H_4$—) and is 1 to 5, in Formula (b) and (c), n is an integer of 1 to 3, in Formulae (a), (b) and (c), $X_1$ is a radioactive halogen atom or —[$^{11}$C]$CH_3$, in Formula (d), $R_3$ is an alkyl group having 1 to 4 carbon atoms that may be substituted with halogen, a hydroxyalkyl group having 1 to 4 carbon atoms, or an alkoxyalkyl group having 1 to 4 carbon atoms, and in Formulae (d) and (e), $R_4$ is a hydrogen atom or a halogen atom.

In one aspect, the present disclosure relates to a compound represented by Formula (2) or a pharmaceutically acceptable salt thereof.

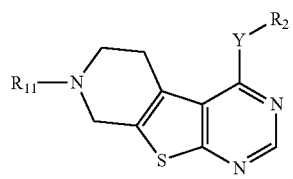
(2)

In Formula (2),
$R_{11}$ is a group represented by Formula (f) or (g):

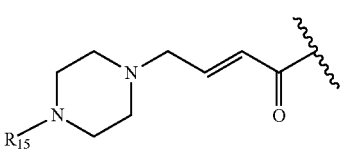

$R_{12}$ is a group represented by Formula (h) or (i):

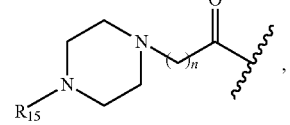

and
Y is —NH— or —O—,
wherein,
in Formulae (f) and (g), $R_{15}$ is a hydrogen atom or -$L_{11}$-X11, wherein $L_{11}$ is an alkanediyl group having 1 to 10 carbon atoms, or

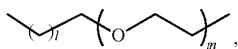

wherein 1 is 0 to 5, and m is the number of repeating ethyleneoxy groups (—OC$_2$H$_4$—) and is 1 to 5, and X$_{11}$ is a chlorine atom, a bromine atom, an iodine atom, a nitro group, a tosylate group, a mesylate group, a triflate group, a nosylate group or a brosylate group, in Formula (g), n is an integer of 1 to 3, in Formula (h), R$_{13}$ is an alkyl group having 1 to 4 carbon atoms that may be substituted with halogen, a hydroxyalkyl group having 1 to 4 carbon atoms, or an alkoxyalkyl group having 1 to 4 carbon atoms, and in Formulae (h) and (i), R$_{14}$ is a hydrogen atom or a halogen atom.

In one aspect, the present disclosure relates to a method for obtaining information for evaluating efficacy of a treatment conducted with an epidermal growth factor receptor tyrosine kinase inhibitor in a subject to be treated for non-small cell lung cancer with the epidermal growth factor receptor tyrosine kinase inhibitor, wherein the method includes detecting a radioactive signal of a nuclear medicine diagnostic imaging agent of the present disclosure from a lung cancer tumor of a subject to which the nuclear medicine diagnostic imaging agent has been administered.

In one aspect, the present disclosure relates to a method for evaluating occurrence of a T790M mutation in a gene that codes for an epidermal growth factor receptor present in the lung cancer tumor, wherein the method includes:

detecting a radioactive signal of a nuclear medicine diagnostic imaging agent of the present disclosure from the lung cancer tumor of a subject to which the nuclear medicine diagnostic imaging agent has been administered, repeating the step of detecting the radioactive signal from the lung cancer tumor of the subject during a treatment conducted with an epidermal growth factor receptor tyrosine kinase inhibitor, comparing the information thus obtained or the radioactive signals thus detected, and determining the presence or absence of the occurrence of a T790M mutation in the gene that codes for the epidermal growth factor receptor in the lung cancer tumor, based on variations in signals obtained by the comparison.

In one aspect, the present disclosure relates to a method for evaluating efficacy of a treatment conducted with an epidermal growth factor receptor tyrosine kinase inhibitor in a subject to be treated for non-small cell lung cancer with the epidermal growth factor receptor tyrosine kinase inhibitor, wherein the method includes comparing the information obtained by the above-described method at two or more times selected from the group consisting of a time before starting the administration of the epidermal growth factor receptor tyrosine kinase inhibitor, a time after starting the administration, and a time after a lapse of a certain period of time after starting the administration.

In one aspect, the present disclosure relates to a compound represented by Formula (3) or a pharmaceutically acceptable salt thereof.

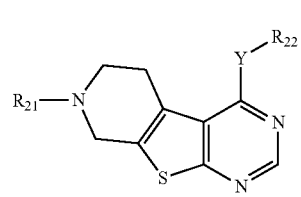

In Formula (3),
R$_{21}$ is a group represented by Formula (j), (k) or (l):

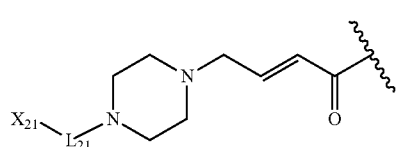

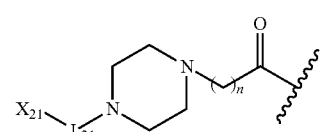

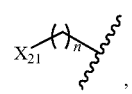

R$_{22}$ is a group represented by Formula (m) or (n):

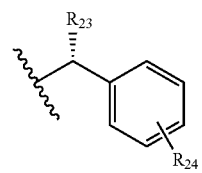

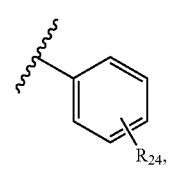

and
Y is —NH— or —O—,
wherein,
in Formulae (j) and (k), L$_{21}$ is a bond, an alkanediyl group having 1 to 10 carbon atoms, or

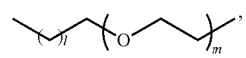

wherein 1 is 0 to 5, and m is the number of repeating ethyleneoxy groups (—OC$_2$H$_4$—) and is 1 to 5,
in Formulae (k) and (l), n is an integer of 1 to 3,
in Formulae (j), (k) and (l), X$_{21}$ is a halogen atom,
in Formula (m), R$_{23}$ is an alkyl group having 1 to 4 carbon atoms that may be substituted with halogen, a hydroxyalkyl group having 1 to 4 carbon atoms, or an alkoxyalkyl group having 1 to 4 carbon atoms, and in Formulae (m) and (n), $R_{24}$ is a hydrogen atom or a halogen atom.

In one aspect, the present disclosure can provide a radioactive labeled compound capable of detecting a secondary mutation of an EGFR and a method for evaluating efficacy of a therapeutic effect of an EGFR-TKI using the same.

BRIEF DESCRIPTION OF THE DRAWINGS

FIG. 1 is a graph showing an example of the results of a cellular uptake experiment.

FIGS. 2A and 2B show images of an example of the results of PET/CT imaging, FIG. 2A showing an image of an example of the result of imaging using a H3255 (L858R mutation) tumor-bearing mouse, and FIG. 2B showing an image of an example of the result of imaging using a H1975 (L858R/T790M mutation) tumor-bearing mouse.

DETAILED DESCRIPTION OF THE INVENTION

In one aspect, the present disclosure is based on the finding that a compound with a tetrahydropyridothieno[2,3-d]pyrimidine skeleton represented by one of Formulae P1 to P10 (Example, Table 1) synthesized in the examples described herein has a relatively high binding affinity to EGFR, especially a L858R-mutated EGFR, but no binding affinity to a L858R/T790M-mutated EGFR. Further, in one aspect, the present disclosure is based on the finding that a radioactive halogen-labeled compound with a tetrahydropyridothieno[2,3-d]pyrimidine skeleton, such as a compound [$^{18}$F]P2 synthesized in the examples described herein, shows a higher adjacent organ ratio (for example tumor/muscle, or tumor/blood) in PET imaging of a H3255 tumor-bearing mouse with a L858R-mutated EGFR and shows a significantly lower adjacent organ ratio (for example tumor/muscle, or tumor/blood) as compared to that of a H3255 tumor-bearing mouse in PET imaging of a H1975 tumor-bearing mouse with a L858R/T790M-mutated EGFR.

In one or more embodiments, a radioactive labeled compound represented by Formula (1) described above can be used to noninvasively determine whether a T790M mutation, which is a secondary mutation, has developed in a lung cancer tumor in which a mutation that increases the sensitivity of an EGFR-TKI, such as an L858R mutation, has developed in an EGFR gene. Furthermore, in one or more embodiments, a radioactive labeled compound represented by Formula (1) can be used to noninvasively determine whether the EGFR-TKI resistance has been acquired in a lung cancer tumor in which a mutation that increases the sensitivity of the EGFR-TKI, such as a L858R mutation, has developed. Moreover, in one or more embodiments, a radioactive labeled compound represented by Formula (1) can be used to evaluate the efficacy of a treatment conducted with an EGFR-TKI in a patient with a lung cancer tumor in which a mutation that increases the sensitivity of the EGFR-TKI, such as a L858R mutation, has developed in an EGFR gene.

In one or more embodiments, the term "capable of detecting a secondary mutation of EGFR" in the present specification includes the ability to discriminate an EGFR in which an L858R mutation (a primary mutation) has occurred from an EGFR in which a T790M mutation (a secondary mutation) has occurred in addition to the L858R mutation.

In the present specification, the term "nuclear medicine diagnostic imaging agent" denotes a pharmacological agent containing a radioactive labeled compound that is used for an in vivo nuclear medicine examination in which a compound with a radioactive isotope (RI) bonded thereto is administered to a body and then the radiation (radioactive signal) emitted from the body is measured and imaged from outside the body and thereby, for example, evaluation or examination of the biological function of an organ or a tissue or disease diagnosis is carried out, or a pharmacological agent containing a radioactive labeled compound that is used for an in vitro nuclear medicine examination in which it is reacted with a sample such as a tissue or blood that was sampled from a body and after which, for example, evaluation or examination of the biological function of an organ or a tissue or disease diagnosis is carried out. In one or more embodiments, examples of the in vivo nuclear medicine examination include methods using a nuclear medical imaging probe such as single photon emission computed tomography (SPECT) and positron emission tomography (PET).

In the present specification, the term "pharmaceutically acceptable salt" includes pharmacologically and/or medicinally acceptable salts. Examples thereof include inorganic acid salts, organic acid salts, inorganic base salts, organic base salts, and acidic or basic amino acid salts. In the present disclosure, the term "salt of a compound" can include a hydrate that can be formed when a compound is exposed to the air to absorb moisture. Furthermore, in the present disclosure, the "salt of a compound" can also include a solvate that can be formed when a compound absorbs another solvent of a certain type.

In the present specification, the term "radioactive halogen atom" denotes a radioactive isotope of a halogen atom. Examples of the radioactive halogen atom include, but are not limited to, $^{123}$I, $^{124}$I, $^{125}$I, $^{131}$I, $^{18}$F, $^{75}$Br, $^{76}$Br, and $^{77}$Br.

In the present specification, the term "alkanediyl group having 1 to 10 carbon atoms" denotes a divalent hydrocarbon group having a branched or straight chain of saturated aliphatics containing 1 to 10 carbon atoms in the straight or branched chain. Examples of the alkanediyl group having 1 to 10 carbon atoms include a methanediyl group, an ethanediyl group, a propanediyl group, a butanediyl group, a pentanediyl group, a hexanediyl group, a heptanediyl group, an octanediyl group, a nonanediyl group, and a decanediyl group.

In the present specification, the term "alkyl group having 1 to 4 carbon atoms that may be substituted with halogen" denotes an alkyl group having 1 to 4 carbon atoms or a halogen-substituted alkyl group having 1 to 4 carbon atoms. The term "alkyl group having 1 to 4 carbon atoms" denotes a monovalent hydrocarbon group having a branched or straight chain of saturated aliphatics containing 1 to 4 carbon atoms in the branched or straight chain. Examples of the alkyl group having 1 to 4 carbon atoms include a methyl group, an ethyl group, a propyl group, and an isopropyl group. The term "halogen-substituted alkyl group having 1 to 4 carbon atoms" denotes an alkyl group having 1 to 4 carbon atoms where one or more hydrogen atoms have been substituted with halogen atoms. Examples of the halogen-substituted alkyl group having 1 to 4 carbon atoms include a monofluoromethyl group, a difluoromethyl group, a trifluoromethyl group, a trifluoroethyl group, and a difluoromethylene group.

In the present specification, the term "hydroxyalkyl group having 1 to 4 carbon atoms" denotes a group where one or more alkyl groups having 1 to 4 carbon atoms have been substituted with hydroxyl groups. Examples of the hydroxyalkyl group having 1 to 4 carbon atoms include a hydroxymethyl group, a hydroxyethyl group, and a hydroxypropyl group.

In the present specification, the term "alkoxyalkyl group having 1 to 4 carbon atoms" denotes a group having 1 to 4 carbon atoms where one or more straight chain or branched alkyl groups have been substituted with alkoxy groups. Examples of the alkoxyalkyl group having 1 to 4 carbon atoms include a methoxymethyl group, an ethoxymethyl group, and a methoxyethyl group.

[Compounds Represented by Formula (1)]

In one or more embodiments, the present disclosure relates to a compound represented by Formula (1) described below or a pharmaceutically acceptable salt thereof (hereinafter referred to as a "compound (1) of the present disclosure"). In one or more embodiments, the compound (1) of the present disclosure exhibits a relatively high binding affinity to a L858R-mutated EGFR but no binding affinity to a T790M-mutated EGFR, which is one of the secondary mutations of an EGFR, and a L858R/T790M-mutated EGFR, which is a double mutant (DM).

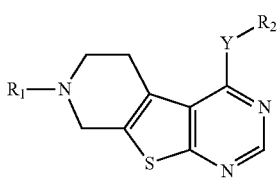
(1)

In Formula (1), $R_1$ is a group represented by Formula (a), (b) or (c).

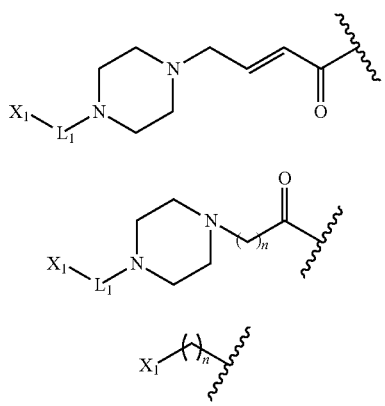

(a)

(b)

(c)

In Formulae (a) and (b), $L_1$ is a bond, an alkanediyl group having 1 to 10 carbon atoms, or

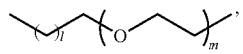

wherein l is 0 to 5, and m is the number of repeating ethyleneoxy groups (—$OC_2H_4$—) and is 1 to 5. In one or more embodiments, examples of $L_1$ include an ethanediyl group, a propanediyl group, a butanediyl group, a pentanediyl group, a hexanediyl group, a methyleneoxyethylene group, an ethyleneoxyethylene group, an ethylenetrioxyethylene group, and an ethylenetetraoxyethylene group. Preferable examples thereof include an ethanediyl group, an ethyleneoxyethylene group (—$C_2H_4$—O—$C_2H_4$— group), and an ethylenetrioxyethylene group (—$C_2H_4$—(O—$C_2H_4$)$_3$— group), in terms of improving the detection of a secondary mutation of an EGFR, preferably in terms of providing a compound having a high binding affinity to a L858R-mutated EGFR and a low binding affinity to a L858R/T790M-mutated EGFR.

In Formulae (b) and (c), n is an integer of 1 to 3, preferably 2 in terms of improving the detection of a secondary mutation of an EGFR, preferably in terms of providing a compound having a high binding affinity to a L858R-mutated EGFR and a low binding affinity to a L858R/T790M-mutated EGFR.

In Formulae (a), (b) and (c), $X_1$ is a radioactive halogen atom or —[$^{11}$C]$CH_3$. In one or more embodiments, $X_1$ is preferably $^{18}$F since it can be used as a PET preparation, has a suitable half-life, and has a relatively small atomic size.

$R_1$ is preferably a group represented by Formula (a) having a Michael acceptor group, more preferably a group represented by Formula (a1) described below, in terms of improving the detection of a secondary mutation of an EGFR, preferably in terms of providing a compound having a high binding affinity to a L858R-mutated EGFR and a low binding affinity to a L858R/T790M-mutated EGFR.

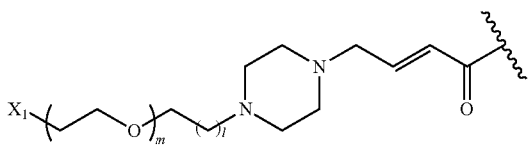
(a1)

In Formula (a1), l is 0 to 5, and in one or more embodiments, 1, 2 or 3. m is the number of repeating ethyleneoxy groups (—$OC_2H_4$—) and is 1 to 5, and in one or more embodiments, 1, 2, 3, 4 or 5.

In Formula (1), $R_2$ is a group represented by Formula (d) or (e).

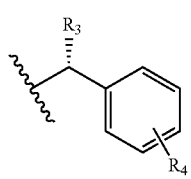
(d)

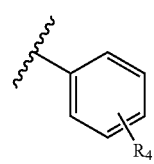
(e)

In Formula (d), $R_3$ is an alkyl group having 1 to 4 carbon atoms that may be substituted with halogen, a hydroxyalkyl group having 1 to 4 carbon atoms, or an alkoxyalkyl group having 1 to 4 carbon atoms. In one or more embodiments, examples of $R_3$ include a methyl group, a trifluoromethyl group, a hydroxymethyl group, and a methoxymethyl group. Preferably, $R_3$ is a methyl group, a hydroxymethyl group, or a methoxymethyl group in terms of improving the detection of a secondary mutation of an EGFR, preferably in terms of providing a compound having a high binding affinity to a L858R-mutated EGFR and a low binding affinity to a L858R/T790M-mutated EGFR.

In Formulae (d) and (e), $R_4$ is a hydrogen atom or a halogen atom, and in one or more embodiments, is a hydrogen atom or a bromine atom.

$R_2$ is preferably a group represented by Formula (d), more preferably a group represented by Formula (d1), (d2) or (d3) described below in terms of improving the detection of a secondary mutation of an EGFR, preferably in terms of providing a compound having a high binding affinity to a L858R-mutated EGFR and a low binding affinity to a L858R/T790M-mutated EGFR.

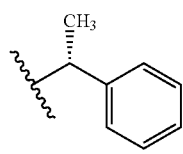
(d1)

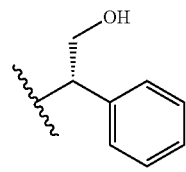
(d2)

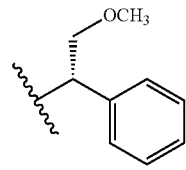
(d3)

In Formula (1), Y is —NH— or —O—.

In one or more embodiments, the compound represented by Formula (1) is preferably a compound represented by Formula (1a) or (1b) described below, more preferably a compound represented by Formula (1c) or (1d) described below where $R_2$ in Formula (1a) or (1b) is a phenylmethylene group having a substituent $R_7$, in terms of improving the detection of a secondary mutation of an EGFR, preferably in terms of making the compound have a high binding affinity to a L858R-mutated EGFR and a low binding affinity to a L858R/T790M-mutated EGFR.

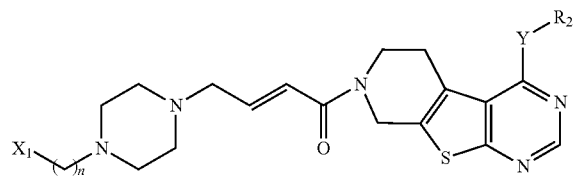
(1a)

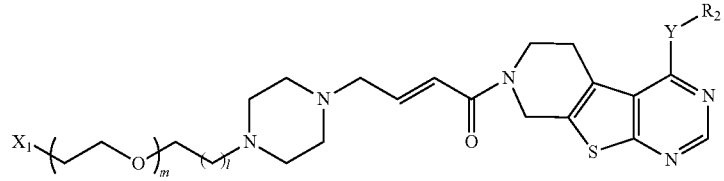
(1b)

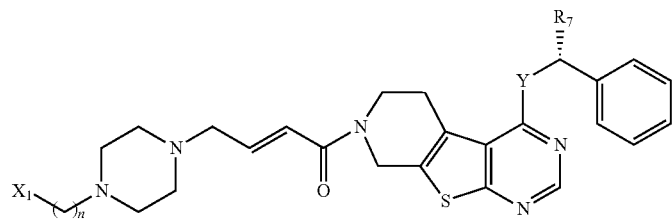
(1c)

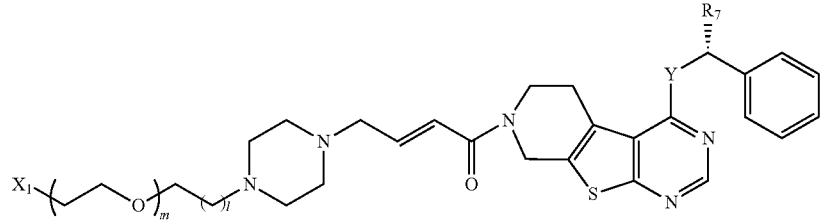
(1d)

In Formulae (1a) to (1d), $X_1$ and Y are as described above. In Formulae (1a) and (1b), $R_2$ is as described above. In Formulae (1b) and (1d), l and m are as described above. In Formulae (1a) and (1c), n is 1 to 10. In Formulae (1c) and (1d), $R_7$ is a methyl group, a hydroxymethyl group or a methoxymethyl group.

In one or more embodiments, examples of the compound represented by Formula (1) include compounds represented by Formulae (1-1) to (1-10) described below and pharmaceutically acceptable salts thereof. The compound represented by Formula (1) is preferably a compound represented by Formula (1-2), (1-5), (1-7), (1-9) or (1-10) in terms of improving the detection of a secondary mutation of an EGFR, preferably in terms of making the compound have a high binding affinity to a L858R-mutated EGFR and a low binding affinity to a L858R/T790M-mutated EGFR. In Formulae (1-1) to (1-10), $X_1$ is a radioactive halogen atom or —[$^{11}$C]$CH_3$, preferably a [$^{18}$F]fluorine atom.

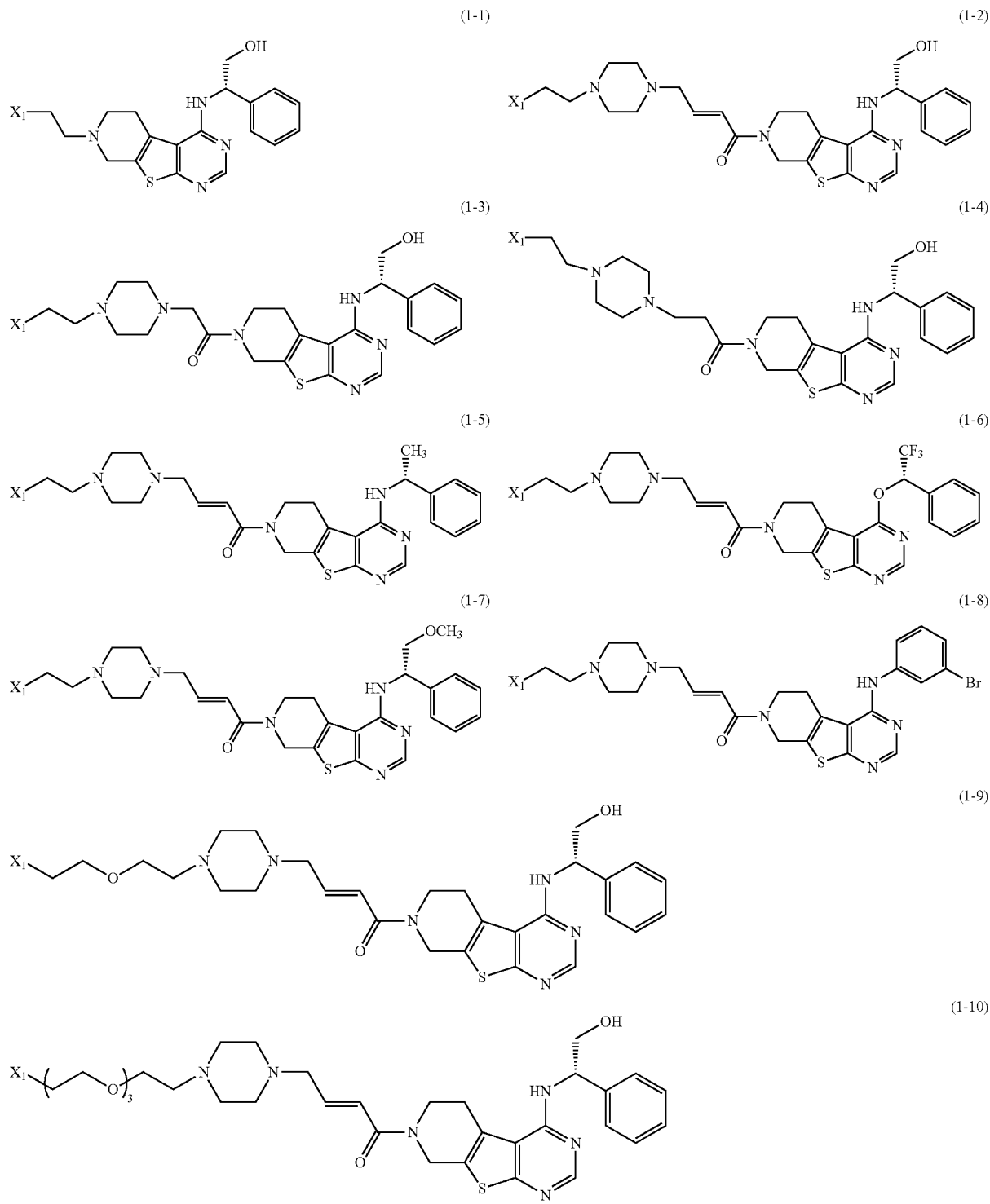

In one or more embodiments, the compound (1) of the present disclosure can be used as an imaging probe, a composition for imaging, a nuclear medicine diagnostic imaging agent (each of which is used for detecting the development of a secondary mutation of EGFR), a diagnostic agent for evaluating the acquisition of an EGFR-TKI resistance, or a diagnostic agent for evaluating efficacy of a treatment conducted with an EGFR-TKI, in a lung cancer tumor in which a mutation that increases the sensitivity of an EGFR-TKI, such as a L858R mutation, has developed, or in a patient with said tumor. In one or more embodiments, therefore, the present disclosure relates to an imaging probe, a composition for imaging, a nuclear medicine diagnostic imaging agent, a diagnostic agent for evaluating the acquisition of an EGFR-TKI resistance, or a diagnostic agent for evaluating efficacy of a treatment conducted with an EGFR-TKI, each of which contains a compound represented by Formula (1) or a pharmaceutically acceptable salt thereof. In one or more embodiments, the present disclosure relates to an imaging probe, a composition for imaging, a nuclear medicine diagnostic imaging agent, a diagnostic agent for evaluating the acquisition of an EGFR-TKI resistance, or a diagnostic agent for evaluating efficacy of a treatment conducted with an EGFR-TKI, each of which contains, as an active ingredient, a compound represented by Formula (1) or a pharmaceutically acceptable salt thereof.

In the present disclosure, the form of the composition for imaging and the various diagnostic agents is not particularly limited but in one or more embodiments, examples of the form include a solution and powder. They may contain pharmaceutical additives such as an acceptable carrier.

[Method for Preparing Compound Represented By Formula (1)]

In one or more embodiments, the compound (1) of the present disclosure can be produced by radioactively labeling a compound represented by Formula (2) described below. In one or more embodiments, therefore, the present disclosure relates to a method for preparing a radioactive compound, including radioactively labeling a compound represented by Formula (2) or a pharmaceutically acceptable salt thereof. Furthermore, in one or more embodiments, the present disclosure relates to a method for preparing a compound represented by Formula (1), including radioactively labeling a compound represented by Formula (2).

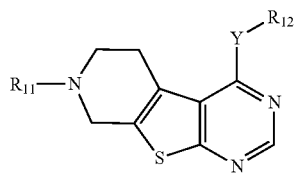

(2)

In Formula (2), $R_{11}$ is a group represented by Formula (f) or (g).

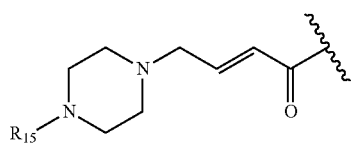

(f)

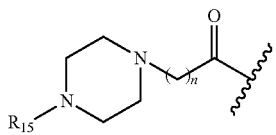

(g)

In Formulae (f) and (g), $R_{15}$ is a hydrogen atom or $-L_{11}-X_{11}$. $L_{11}$ is an alkanediyl group having 1 to 10 carbon atoms, or

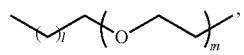

wherein l is 0 to 5, and m is the number of repeating ethyleneoxy groups ($-OC_2H_4-$) and is 1 to 5. Examples of $L_{11}$ include the same as those of $L_1$ in Formula (1).

$X_{11}$ is a chlorine atom, a bromine atom, an iodine atom, a nitro group, a tosylate group, a mesylate group, a triflate group, a nosylate group or a brosylate group.

In Formula (g), n is an integer of 1 to 3, preferably 2 in terms of improving the detection of a secondary mutation of an EGFR, preferably in terms of providing a compound having a high binding affinity to a L858R-mutated EGFR and a low binding affinity to a L858R/T790M-mutated EGFR.

$R_{11}$ is preferably a group represented by Formula (f), more preferably a group represented by Formula (f1) or (f2) described below in terms of providing a labeled compound with improved detection of a secondary mutation of an EGFR, preferably in terms of providing a labeled compound having a high binding affinity to a L858R-mutated EGFR and a low binding affinity to a L858R/T790M-mutated EGFR.

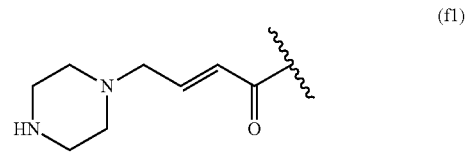

(f1)

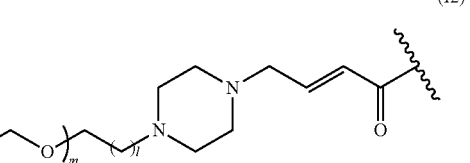

(f2)

In Formula (f2), l is 0 to 5, and in one or more embodiments, 1, 2 or 3. m is the number of repeating ethyleneoxy groups ($-OC_2H_4-$) and is 1 to 5, and in one or more embodiments, 1, 2, 3, 4 or 5.

In Formula (2), $R_{12}$ is a group represented by Formula (h) or (i).

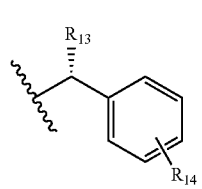

(h)

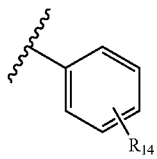
(i)

In Formula (h), $R_{13}$ is an alkyl group having 1 to 4 carbon atoms that may be substituted with halogen, a hydroxyalkyl group having 1 to 4 carbon atoms, or an alkoxyalkyl group having 1 to 4 carbon atoms. Examples of $R_{13}$ include the same as those of $R_3$ in Formula (1).

In Formulae (h) and (i), $R_{14}$ is a hydrogen atom or a halogen atom. Examples of $R_{14}$ include the same as those of $R_4$ in Formula (1).

Preferable examples of $R_{12}$ include the same as those of $R_2$ in Formula (1).

In Formula (2), Y is —NH— or —O—.

In one or more embodiments, the compound represented by Formula (2) is preferably a compound represented by Formula (2-1) or (2-2) described below, more preferably a compound represented by Formula (2-3) or (2-4) described below where $R_{12}$ in Formula (2-1) or (2-2) is a phenylmethylene group having a substituent $R_{17}$, in terms of providing a labeled compound with improved detection of a secondary mutation of an EGFR, preferably in terms of providing a labeled compound having a high binding affinity to a L858R-mutated EGFR and a low binding affinity to a L858R/T790M-mutated EGFR.

In Formulae (2-3) and (2-4), $R_{17}$ is a methyl group, a hydroxymethyl group or a methoxymethyl group. In Formulae (2-1) to (2-4), Y and $R_{12}$ are as described above. In Formulae (2-2) and (2-4), 1 and m are as described above.

The method for radioactively labeling a compound represented by Formula (2) can be determined suitably according to the structure of the compound represented by Formula (2). In one or more embodiments, when $R_{15}$ is $-L_{11}-X_{11}$ in Formula (2), the compound can be labeled using a direct labeling method. When $R_{15}$ is a hydrogen atom in Formula (2), for example, $X_1$-L11-$X_{11}$ can be used to label the compound using an indirect labeling method. $X_1$ and $X_{11}$ are as described above.

As described above, the compound represented by Formula (2) can be used as a labeling precursor (i.e., an unlabeled compound used for a radioactive labeling). In one or more embodiments, therefore, the present disclosure relates to a compound represented by Formula (2) or a pharmaceutically acceptable salt thereof (hereinafter referred to as a "compound (2) of the present disclosure"). Furthermore, in one or more embodiments, the present disclosure relates to a composition containing a compound (2) of the present disclosure that is used as a labeling precursor for synthesizing a compound (1) of the present disclosure. Moreover, in one or more embodiments, the present disclosure relates to a kit for preparing a compound (1) of the present disclosure containing a compound (2) of the present disclosure. In one or more embodiments, the kit of the present disclosure may further include a labeling reagent containing a radioactive halogen atom.

(2-1)
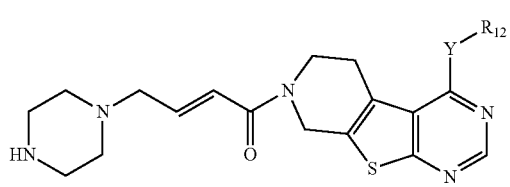

(2-2)
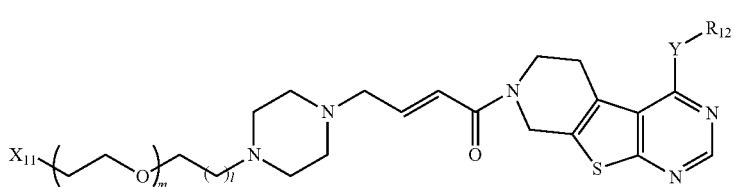

(2-3)
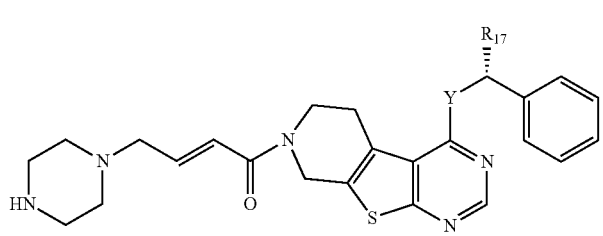

(2-4)
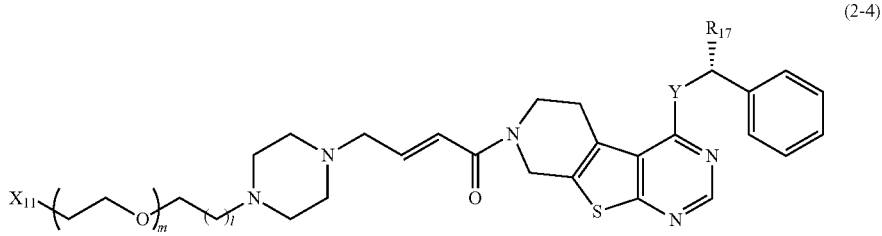

[Method for Obtaining Information for Evaluating Efficacy of Treatment Conducted with an EGFR-TKI]

In one or more embodiments, the present disclosure relates to a method for obtaining information for evaluating efficacy of a treatment to be conducted with an EGFR-TKI in a subject to be treated for non-small cell lung cancer with the EGFR-TKI (hereinafter also referred to as a "method for obtaining information of the present disclosure"). The subject is not particularly limited but in one or more embodiments, the subject is selected from human beings, mammals other than human beings, cultured cells, and subjects in which EGFR may exist.

In one or more embodiments, the method for obtaining information of the present disclosure includes detecting a radioactive signal of a compound (1) of the present disclosure or a nuclear medicine diagnostic imaging agent containing a compound (1) of the present disclosure from a lung cancer tumor of a subject to which the compound (1) of the present disclosure or the nuclear medicine diagnostic imaging agent has been administered. The method for detecting the signal can be determined suitably according to the type of the radioisotope contained in the compound of the present disclosure to be used and can be carried out using, for example, PET or SPECT. In one or more embodiments, examples of the information or data include radioactive signals that are detected.

In one or more embodiments, the method for obtaining information of the present disclosure includes repeating the detection of the radioactive signal from a lung cancer tumor of the subject during the treatment conducted with an EGFR-TKI.

In one or more embodiments, examples of the EGFR-TKI to be used for the treatment include a reversible EGFR-TKI. In one or more embodiments, examples of the reversible EGFR-TKI include gefitinib and erlotinib.

[Method for Evaluating Occurrence of Secondary Mutation of EGFR]

In one or more embodiments, the present disclosure relates to a method for evaluating occurrence of a T790M mutation in a gene that codes for an epidermal growth factor receptor in a lung cancer tumor. In one or more embodiments, the evaluation method of the present disclosure includes: detecting a radioactive signal of a nuclear medicine diagnostic imaging agent of the present disclosure from the lung cancer tumor of a subject to which the nuclear medicine diagnostic imaging agent has been administered; repeating the step of detecting the radioactive signal from the lung cancer tumor of the subject during a treatment conducted with an EGFR-TKI; comparing the information thus obtained; and determining the presence or absence of the occurrence of a T790M mutation in the gene that codes for the EGFR in the lung cancer tumor, based on variations in the signals obtained by the comparison.

[Method for Evaluating Efficacy of Treatment Conducted with an EGFR-TKI]

In one or more embodiments, the present disclosure relates to a method for evaluating efficacy of a treatment to be conducted with an EGFR-TKI in a subject to be treated for non-small cell lung cancer with the EGFR-TKI (hereinafter also referred to as an "evaluation method of the present disclosure").

In one or more embodiments, the evaluation method of the present disclosure includes comparing the information obtained by the method for obtaining information of the present disclosure at two or more times selected from the group consisting of a time before starting the administration of an EGFR-TKI, a time after starting the administration, and a time after a lapse of a certain period of time after starting the administration.

In one or more embodiments, the evaluation method of the present disclosure may include determining, based on variations in the signals obtained by the comparison, whether a T790M mutation has developed in a gene that codes for the epidermal growth factor receptor in a lung cancer tumor. Furthermore, in one or more embodiments of the evaluation method of the present disclosure, when a reduction in the signals is observed by the comparison, it can be determined that the possibility of the efficacy of the treatment conducted with an EGFR-TKI is reduced, while when a reduction in the signals is not observed by the comparison, it can be determined that the possibility of the pharmacological efficacy of the treatment conducted with an EGFR-TKI exists. Furthermore, in one or more embodiments of the evaluation method of the present disclosure, when the size of the tumor increases or is maintained while the reduction in the signals is observed, it can be determined that the possibility of the pharmacological efficacy of the treatment conducted with the EGFR-TKI is reduced.

In one or more embodiments, the evaluation method of the present disclosure may include obtaining a CT or MRI image of the subject and fusing the CT or MRI image and an imaging picture constructed from the radioactive signals detected above or comparing them with each other. Furthermore, in one or more embodiments of the evaluation method of the present disclosure, based on the above-mentioned fusion or comparison, when the size of the tumor increases or is maintained while the reduction in the signals is observed, it can be determined that the possibility of the pharmacological efficacy of the treatment conducted with an EGFR-TKI is reduced.

[Method for Imaging EGFR-Positive Lung Cancer Tumor]

In one or more embodiments, the present disclosure relates to an imaging method including detecting a radioactive signal of a compound (1) of the present disclosure from a subject to which the compound has been administered.

[Compound Represented by Formula (3)]

In one or more embodiments, the present disclosure relates to a compound represented by Formula (3) or a pharmaceutically acceptable salt thereof.

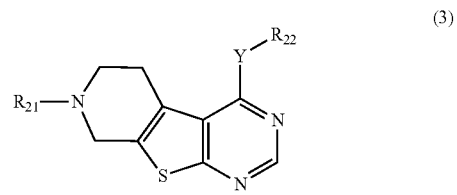

(3)

In Formula (3), $R_{21}$ is a group represented by Formula (j), (k) or (l):

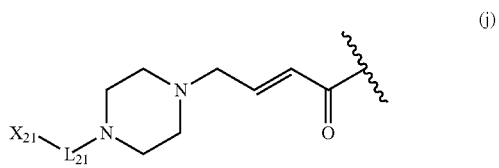

(j)

-continued

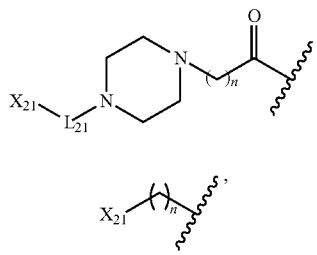
(k)

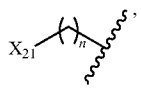
(l)

$R_{22}$ is a group represented by Formula (m) or (n):

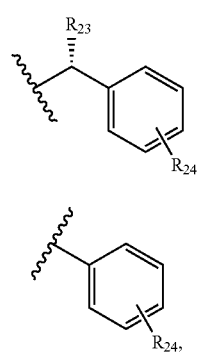
(m)

(n)

and
Y is —NH— or —O—,
wherein,
in Formulae (j) and (k), $L_{21}$ is a bond, an alkanediyl group having 1 to 10 carbon atoms, or

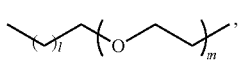

wherein l is 0 to 5, and m is the number of repeating ethyleneoxy groups (—OC$_2$H$_4$—) and is 0 to 5,
in Formulae (k) and (l), n is an integer of 1 to 3,
in Formulae (j), (k) and (l), $X_{21}$ is a halogen atom,
in Formula (m), $R_{23}$ is an alkyl group having 1 to 4 carbon atoms that may be substituted with halogen, a hydroxyalkyl group having 1 to 4 carbon atoms, or an alkoxyalkyl group having 1 to 4 carbon atoms, and
in Formulae (m) and (n), $R_{24}$ is a hydrogen atom or a halogen atom.

In one or more embodiments, the compound represented by Formula (3) exhibits a relatively high binding affinity to a L858R-mutated EGFR but no binding affinity to a T790M-mutated EGFR, which is one of the secondary mutations of an EGFR, and a L858R/T790M-mutated EGFR, which is a double mutant (DM). $L_{21}$, $R_{22}$, and n are the same as $L_1$, $R_2$, and n in Formula (1), respectively.

The present disclosure may relate to one or more embodiments described below.

<1> A nuclear medicine diagnostic imaging agent, including a compound represented by Formula (1) or a pharmaceutically acceptable salt thereof.

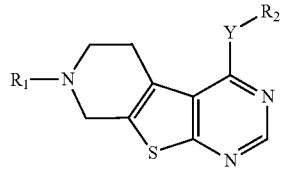
(1)

In Formula (1),
$R_1$ is a group represented by Formula (a), (b) or (c):

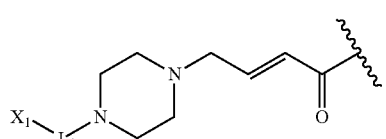
(a)

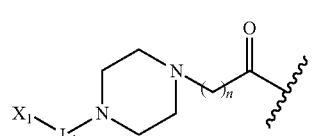
(b)

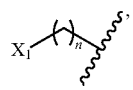
(c)

$R_2$ is a group represented by Formula (d) or (e):

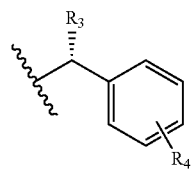
(d)

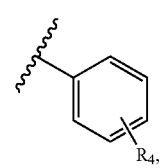
(e)

and
Y is —NH— or —O—,
wherein,
in Formulae (a) and (b), $L_1$ is a bond, an alkanediyl group having 1 to 10 carbon atoms, or

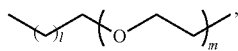

wherein l is 0 to 5, and m is the number of repeating ethyleneoxy groups (—OC$_2$H$_4$—) and is 1 to 5,
in Formulae (b) and (c), n is an integer of 1 to 3,
in Formulae (a), (b) and (c), $X_1$ is a radioactive halogen atom or —[$^{11}$C]CH$_3$,
in Formula (d), $R_3$ is an alkyl group having 1 to 4 carbon atoms that may be substituted with halogen, a hydroxyalkyl group having 1 to 4 carbon atoms, or an alkoxyalkyl group having 1 to 4 carbon atoms, and
in Formulae (d) and (e), $R_4$ is a hydrogen atom or a halogen atom.

<2> The nuclear medicine diagnostic imaging agent according to <1>, wherein $L_1$ is an ethanediyl group, an ethyleneoxyethylene group, or an ethylenetrioxyethylene group.

<3> The nuclear medicine diagnostic imaging agent according to <1> or <2>, wherein $R_3$ is a methyl group, a trifluoromethyl group, a hydroxymethyl group, or a methoxymethyl group.

<4> The nuclear medicine diagnostic imaging agent according to any one of <1> to <3>, wherein $R_4$ is a hydrogen atom or a bromine atom.

<5> A compound represented by Formula (1) or a pharmaceutically acceptable salt thereof.

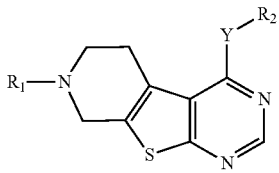
(1)

In Formula (1), $R_1$ is a group represented by Formula (a), (b) or (c):

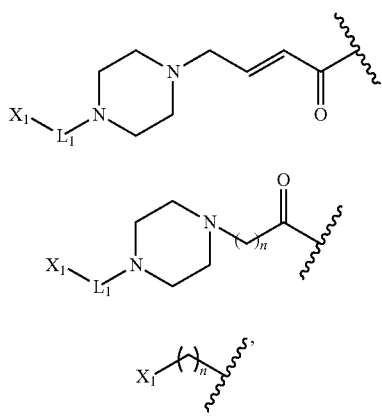
(a)
(b)
(c)

$R_2$ is a group represented by Formula (d) or (e):

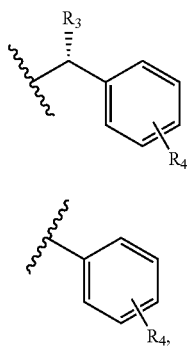
(d)
(e)

and

Y is —NH— or —O—, wherein, in Formulae (a) and (b), $L_1$ is a bond, an alkanediyl group having 1 to 10 carbon atoms, or

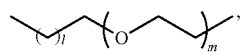

wherein l is 0 to 5, and m is the number of repeating ethyleneoxy groups ($—OC_2H_4—$) and is 1 to 5, in Formula (b) and (c), n is an integer of 1 to 3, in Formulae (a), (b) and (c), $X_1$ is a radioactive halogen atom or $—[^{11}C]CH_3$, in Formula (d), $R_3$ is an alkyl group having 1 to 4 carbon atoms that may be substituted with halogen, a hydroxyalkyl group having 1 to 4 carbon atoms, or an alkoxyalkyl group having 1 to 4 carbon atoms, and in Formulae (d) and (e), $R_4$ is a hydrogen atom or a halogen atom.

<6> A compound represented by Formula (2) or a pharmaceutically acceptable salt thereof.

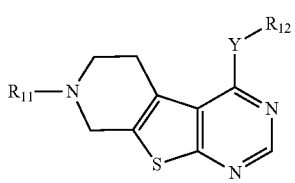
(2)

In Formula (2), $R_{11}$ is a group represented by Formula (f) or (g):

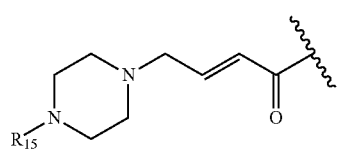
(f)
(g)

$R_{12}$ is a group represented by Formula (h) or (i):

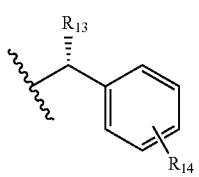
(h)

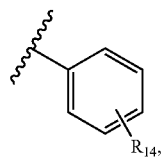

and
Y is —NH— or —O—,
wherein,
in Formulae (f) and (g), $R_{15}$ is a hydrogen atom or $-L_{11}-X_{11}$, wherein $L_{11}$ is an alkanediyl group having 1 to 10 carbon atoms, or

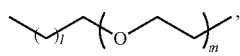

wherein l is 0 to 5, and m is the number of repeating ethyleneoxy groups (—$OC_2H_4$—) and is 1 to 5, and $X_{11}$ is a chlorine atom, a bromine atom, an iodine atom, a nitro group, a tosylate group, a mesylate group, a triflate group, a nosylate group or a brosylate group,
in Formula (g), n is an integer of 1 to 3,
in Formula (h), $R_{13}$ is an alkyl group having 1 to 4 carbon atoms that may be substituted with halogen, a hydroxyalkyl group having 1 to 4 carbon atoms, or an alkoxyalkyl group having 1 to 4 carbon atoms, and
in Formulae (h) and (i), $R_{14}$ is a hydrogen atom or a halogen atom.
<7> The compound according to <6>, wherein $R_{15}$ is a hydrogen atom.
<8> A composition containing a compound according to <6> or <7> for use as a labeling precursor for synthesizing a nuclear medicine diagnostic imaging agent according to any one of <1> to <4>.
<9> A method for obtaining information for evaluating efficacy of a treatment conducted with an EGFR-TKI in a subject to be treated for non-small cell lung cancer with the EGFR-TKI,
wherein the method includes detecting a radioactive signal of a nuclear medicine diagnostic imaging agent according to any one of <1> to <4> from a lung cancer tumor of the subject to which the nuclear medicine diagnostic imaging agent has been administered.
<10> The method according to <9>, wherein the method includes repeating the step of detecting the radioactive signal from the lung cancer tumor of the subject during the treatment conducted with the EGFR-TKI.
<11> A method for evaluating occurrence of a T790M mutation in a gene that codes for an EGFR in a lung cancer tumor,
wherein the method includes:
detecting a radioactive signal of a nuclear medicine diagnostic imaging agent according to any one of <1> to <4> from the lung cancer tumor of a subject to which the nuclear medicine diagnostic imaging agent has been administered,
repeating the step of detecting the radioactive signal from the lung cancer tumor of the subject during a treatment conducted with an EGFR-TKI,
comparing the information thus obtained, and
determining the presence or absence of the occurrence of a T790M mutation in the gene that codes for the EGFR in the lung cancer tumor, based on variations in the signals obtained by the comparison.
<12> A method for evaluating efficacy of a treatment conducted with an EGFR-TKI in a subject to be treated for non-small cell lung cancer with the EGFR-TKI,
wherein the method includes comparing information obtained by a method according to <9> or <10> at two or more times selected from the group consisting of a time before starting the administration of the EGFR-TKI, a time after starting the administration, and a time after a lapse of a certain period of time after starting the administration.
<13> The method according to <12>, wherein the method includes determining, based on variations in the signals obtained by the comparison, whether a gene that codes for an EGFR in a lung cancer tumor has a T790M mutation.
<14> The method according to <12> or <13>, wherein when a reduction in the signals is observed by the comparison, it is determined that the possibility of pharmacological efficacy of the treatment conducted with the EGFR-TKI is reduced, while when a reduction in the signals is not observed by the comparison, it is determined that the possibility of pharmacological efficacy of the treatment conducted with the EGFR-TKI exists.
<15> The method according to <12> or <13>, wherein when the size of the tumor increases or is maintained while the reduction in the signals is observed, it is determined that the possibility of the pharmacological efficacy of the treatment conducted with the EGFR-TKI is reduced.
<16> The method according to any one of <12> to <15>, wherein the method includes:
imaging a CT or MRI image of the subject, and
fusing the CT or MRI image and an imaging picture constructed from the radioactive signals that have been detected or comparing them with each other, and
based on the fusion or comparison, when the size of the tumor increases or is maintained while the reduction in the signals is observed, it is determined that the possibility of the pharmacological efficacy of the treatment conducted with the EGFR-TKI is reduced.

<17> A compound represented by Formula (3) or a pharmaceutically acceptable salt thereof.

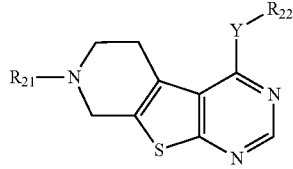  (3)

In Formula (3), $R_{21}$ is a group represented by Formula (j), (k) or (l):

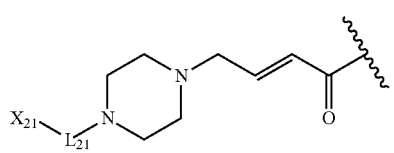  (j)

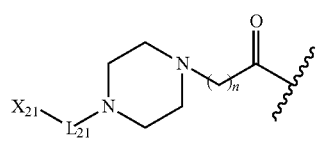  (k)

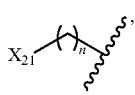  (l)

$R_{22}$ is a group represented by Formula (m) or (n):

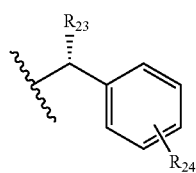  (m)

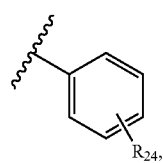  (n)

and

Y is —NH— or —O—, wherein, in Formulae (j) and (k), $L_{21}$ is a bond, an alkanediyl group having 1 to 10 carbon atoms, or

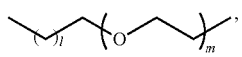

wherein l is 0 to 5, and m is the number of repeating ethyleneoxy groups (—OC$_2$H$_4$—) and is 1 to 5, in Formulae (k) and (l), n is an integer of 1 to 3, in Formulae (j), (k) and (l), $X_{21}$ is a halogen atom, in Formula (m), $R_{23}$ is an alkyl group having 1 to 4 carbon atoms that may be substituted with halogen, a hydroxyalkyl group having 1 to 4 carbon atoms, or an alkoxyalkyl group having 1 to 4 carbon atoms, and in Formulae (m) and (n), $R_{24}$ is a hydrogen atom or a halogen atom.

<18> A kit for preparing a compound according to <5>, including a compound according to <6> or <7> or a composition according to <8>.

EXAMPLES

Hereinafter, the present disclosure is further described by way of examples. However, they are illustrative and the present disclosure shall not be interpreted to be limited to the following examples.

[Apparatuses and Reagents]

Mass spectrometry (ESI-MS) was measured with LCMS-2010 EV (Shimadzu Corporation).

$^1$H (400 MHz or 500 MHz) NMR spectrum was measured with LNM-AL 400 or 500 (JEOL Ltd.), and tetramethylsilane was used as an internal standard substance.

LC-20AD (Shimadzu Corporation) was used for reversed-phase HPLC, and SPD-20A UV (Shimadzu Corporation) and a survey meter NDW-351 (Hitachi, Ltd. (formerly Hitachi Aloka Medical, Ltd.)) were used as detectors. The reversed-phase HPLC columns used herein were COSMOSIL C$_{18}$-AR-II (4.6×250 mm) and COSMOSIL C$_{18}$-AR-II (10×250 mm) (Nacalai Tesque, Inc.), and the mobile phases used herein were (A) a 0.1% TFA aqueous solution, and (B) a 0.1% TFA acetonitrile solution. Silica gel 60 F254 (Merck Ltd., Japan) was used for TLC.

An intermediate pressure column W-Prep 2XY (Yamazen Corporation) was used for purification by column chromatography, and the silica gel used herein was Hi Flash silica gel 40 mm, 60 Å (Yamazen Corporation).

[$^{18}$F]fluoride was produced using [$^{18}$O]H$_2$O (Taiyo Nippon Sanso Corporation) and CYPRIS HM-18 Cyclotron (Sumitomo Heavy Industries, Ltd.) installed at Kyoto University Hospital.

A microwave reactor (Saida FDS Inc.) was used to synthesize radioactive compounds. Radioactivity was measured using a curie-meter IGC-7 (Hitachi, Ltd.) and an auto well gamma counter Wallac 1480 WIZARD 3 (PerkinElmer).

Image acquisition by a PET device was carried out using a GMI FX-3300 Pre-Clinical Imaging System.

[Synthesis of Compounds]

(Step A)

Synthesis of Tetrahydropyridothieno-[2,3-d]pyrimidine skeleton (Compound 4)

Compound 4 was synthesized according to a technique reported by Hsien et al. (Wu, C. H. bb et al., Design and Synthesis of Tetrahydropyridothieno[2,3-d]pyrimidine Scaffold Based Growth Factor Receptor (EGFR) Kinase Inhibitors: The Role of Side Chain and Michael Acceptor Group for Maximal Potency. J. Med. Chem. 2010, 53, 7316-7326.)

(Scheme 1)
Scheme 1. Synthesis of a tetrahydropyridothieno[2,3-d]pyrimidine scaffold EGFR-TKI.

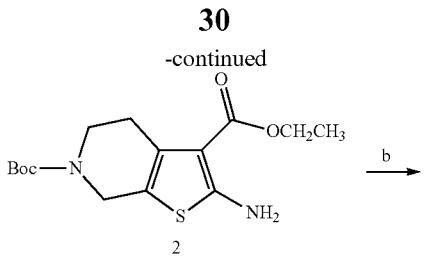

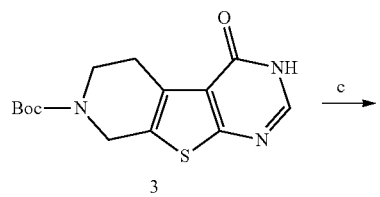

[1] Reagents and conditions: (a) cyano ethylacetate, S₈, Et₃N in EtOH; (b) formamidine acetate in DMF, 100° C., (c) POCl₃, Et₃N, 0→60° C.

Step B

Synthesis of Compounds 8-13 (P2-7)

Compounds 8-13 (P2-7) were synthesized according to the following scheme 2.

Scheme 2. Synthesis of compounds 1-7 (Cold form) containing tetrahydropyridothieno[2,3-d]pyrimidine scaffold.

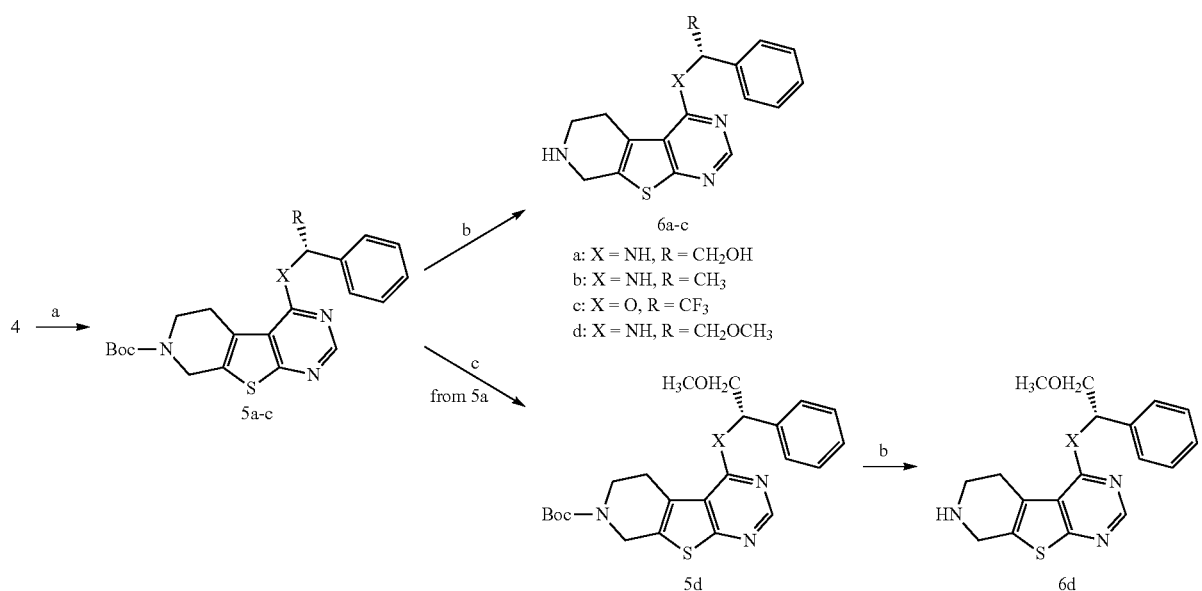

a: X = NH, R = CH₂OH
b: X = NH, R = CH₃
c: X = O, R = CF₃
d: X = NH, R = CH₂OCH₃

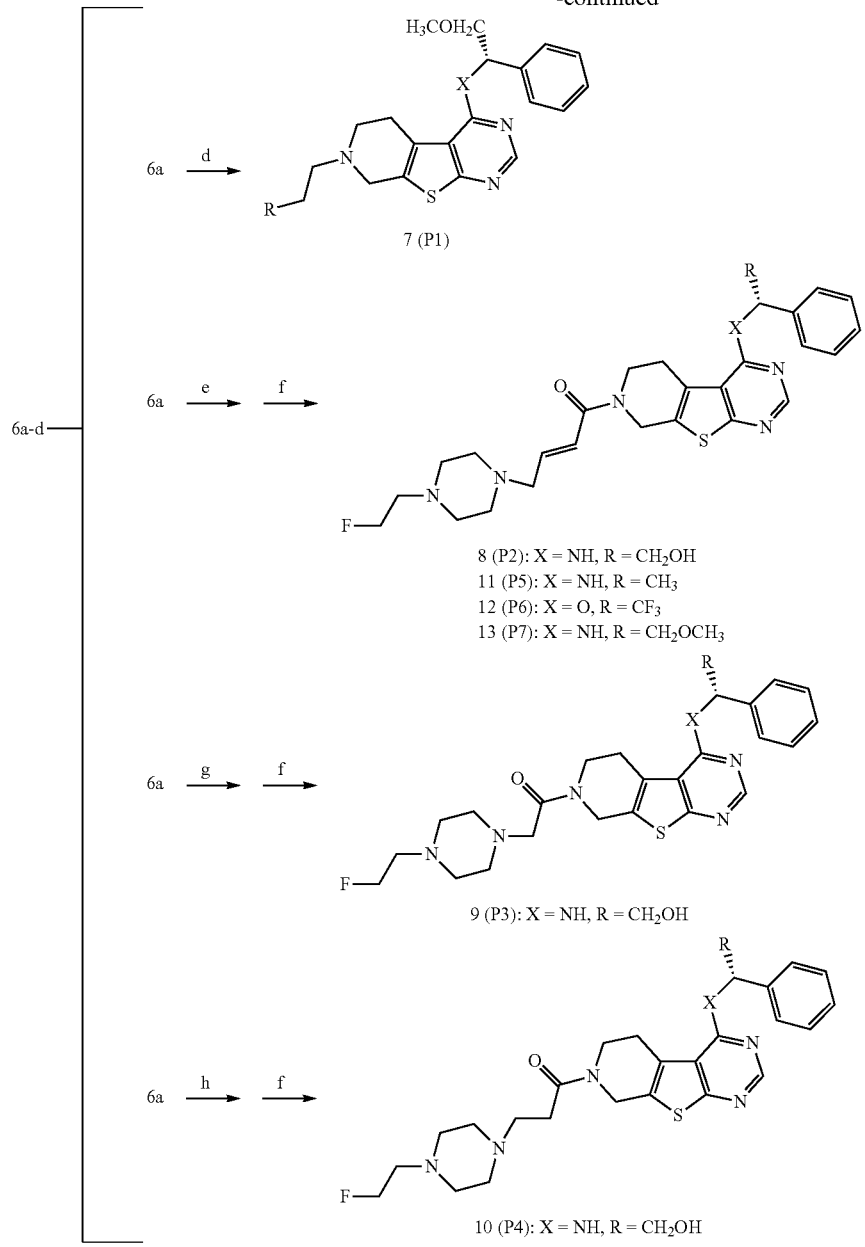

Reagents and conditions: (a) (S)-(+)-2-amino-2-phenylethanol, (R)-(+)-1-phenylethylamine or (S)-(+)-1-phenyl-2,2,2-trifluoroethanol in EtOH, reflux; (b) 4M HCl/dioxane; (c) NaH, CH₃I in THF; (d) 2-fluoroethyl-4-toluene sulfonate, Cs₂CO₃ in DMF, 60° C.; (e) 4-bromo crotonic acid, IBCF, Et₃N in THF, -15° C.→r.t.; (f) 1-(2-fluoroethyl)piperazine, Et₃N; (g) 2-bromo ethanoic acid, IBCF, Et₃N in THF, -15° C.→r.t.; (h) 3-bromo propanoic acid, IBCF, Et₃N in THF, -15° C.→r.t..

Various side chains were introduced into the chloro group of Compound 4, and thereby Compound 5a-c was obtained (scheme 2). The hydroxyl group in the side chain of Compound 5a was methylated, and thereby Compound 5d was obtained.

Synthesis of Compound 5a-c

Compound 4 (1.77 mmol), together with corresponding amine or alcohol, was heated and refluxed in alcohol (40 mL) overnight at 100° C. The solvent after reaction was evaporated to dryness, and the residue was purified by column chromatography.

tert-Butyl (S)-4-((2-hydroxy-1-phenylethyl)amino)-5,8-dihydropyrido[4',3':4,5]thieno[2,3-d]pyrimidine-7 (6H)carboxylate (Compound 5a)

Compound 4 and (S)-(+)-2-amino-2-phenylethanol were heated and refluxed in ethanol, and thereby Compound 5a was obtained. Yield 732 mg (97.1%), $^1$H NMR (500 MHz, DMSO-$d_6$) δ8.14 (1H, s), 7.36 (2H, d, J=7.4 Hz), 7.22 (2H, t, J=7.6 Hz), 7.13 (1H, t, J=7.3 Hz), 6.46 (1H, d, J=7.4 Hz), 5.29 (1H, q, J=5.9 Hz), 5.15 (1H, t, J=5.6 Hz), 4.56 (2H, d, J=5.7 Hz), 3.78-3.66 (4H, m), 3.10 (2H, s), 1.37 (9H, s).

tert-Butyl (R)-4-((1-phenylethyl)amino)-5,8-dihydropyrido[4',3':4,5]thieno[2,3-d]pyrimidine-7(6H)carboxylate (Compound 5b)

Compound 4 and (R)-(+)-1-phenylethylamine were heated and refluxed in ethanol, and thereby Compound 5b was obtained. Yield 102 mg (81.1%), $^1$H NMR (500 MHz, CDCl$_3$) δ8.40 (1H, s), 7.40-7.26 (5H, m), 5.55 (1H, br), 5.39 (1H, br), 4.65 (1H, br), 1.63 (2H, d, J=6.6 Hz), 1.49 (9H, s).

tert-Butyl (S)-4-(2,2,2-trifluoro-1-phenylethoxy)-5, 8-dihydropyrido [4',3':4,5]thieno[2,3-d]pyrimidine-7 (6H)carboxylate (Compound 5c)

Compound 4 and (S)-(+)-1-phenyl-2,2,2-trifluoroethanol were heated and refluxed in ethanol, and thereby Compound 5c was obtained. Yield 137 mg (95.4%), $^1$H NMR (400 MHz, CDCl$_3$) δ8.49 (1H, s), 7.59-7.38 (5H, m), 6.84 (1H, q, J=6.8 Hz), 4.78-4.64 (2H, m), 3.94-3.76 (2H, m), 3.21 (2H, br), 1.52 (9H, s).

tert-Butyl (S)-4((2-methoxy-1-phenylethyl)amino)-5,8-dihydropyrido[4',3':4,5]thieno[2,3-d]pyrimidine-7(6H)carboxylate (Compound 5d)

Compound 5a (300 mg, 0.704 mmol) was dissolved in anhydrous THF (7 mL), to which sodium hydride (52.0 mg, 1.41 mmol, 60% oiliness) was added slowly at 0° C. After a lapse of 15 minutes, methyl iodide (48.2 mL, 0.774 mmol) was added thereto and stirred overnight at room temperature. The reaction solution was neutralized with a saturated ammonium chloride aqueous solution at 0° C. and extracted with ethyl acetate. The organic layer was collected and dried with sodium sulfate. Thereafter, the solvent was evaporated to dryness. The residue thus obtained was purified by column chromatography. Yield 123 mg (24.9%), $^1$H NMR (400 MHz, CDCl$_3$) δ8.33 (1H, s), 7.41-7.27 (5H, m), 6.14 (1H, br), 5.55 (1H, br), 4.72-4.64 (2H, m), 3.83-3.77 (4H, m), 3.41 (3H, s), 3.10 (2H, br), 1.51 (9H, s).

Synthesis of Compound 6a-d

4M HCl/dioxane (150 mL, 0.610 mmol) was added to Compound 5a-d (1.12 mmol) at 0° C., followed by reaction at room temperature for one hour. The reaction solution was mixed with water and neutralized with a sodium hydrogencarbonate aqueous solution at 0° C. and extracted with ethyl acetate. The organic layer was collected and dried with sodium sulfate. Thereafter, the solvent was evaporated to dryness.

(S)-2-Phenyl-2-((5, 6, 7, 8-tetrahydropyrido[4',3':4, 5]thieno[2, 3-d]pyrimidin-4-yl)amino)ethan-1-ol (Compound 6a)

Compound 6a was prepared using Compound 5a as a material. Yield 68.6 mg (89.7%), LCMS (ESI): m/z 327.05 [M+H]$^+$.

(R)—N-(1-Phenylethyl)-5,6,7,8-tetrahydropyrido[4', 3':4,5]thieno[2,3-d]pyrimidin-4-amine (Compound 6b)

Compound 6b was prepared using Compound 5b as a material. Yield 35.5 mg (93.9%), LCMS (ESI): m/z 311.13 [M+H]$^+$.

(S)-4-(2,2,2-Trifluoro-1-phenylethoxy)-5, 6, 7, 8-tetrahydropyrido[4',3':4,5]thieno[2, 3-d]pyrimidine (Compound 6c)

Compound 6c was prepared using Compound 5c as a material. Yield 107 mg (98.9%), LCMS (ESI): m/z 406.95 [M+H+CH$_3$CN]$^+$.

(S)—N-(2-Methoxy-1-phenylethyl)-5,6,7,8-tetrahydropyrido[4',3':4,5]thieno[2,3-d]pyrimidin-4-amine (Compound 6d)

Compound 6d was prepared using Compound 5d as a material. Yield 30.0 mg (64.7%), LCMS (ESI): m/z 340.95 [M+H]$^+$.

Synthesis of (S)-2-((7-Fluoroethyl)-5,6,7,8-tetrahydropyrido[4',3':4,5]thieno[2,3-d]pyrimidin-4-yl) amino)-2-phenylethan-1-ol (Compound 7: P1)

Compound 6a (124 mg, 0.381 mmol) was dissolved in anhydrous DMF (2 mL), and Cs$_2$CO$_3$ (124 mg, 0.381 mmol) and 2-fluoroethyl tosylate (83.2 mg, 0.381 mmol) were added thereto, followed by stirring overnight at 60° C. and stirring one more night at room temperature. The reaction solution was poured into water and neutralized with chloroform. The organic layer was washed with saturated saline and dried with sodium sulfate. The solvent was evaporated to dryness, and the residue thus obtained was preparatively purified by reversed-phase HPLC. Yield 7.00 mg (4.92%), $^1$H NMR (500 MHz, DMSO-d$_6$) δ8.28 (1H, s), 7.43 (2H, d, J=7.4 Hz), 7.31 (2H, t, J=7.4 Hz), 7.23 (1H, t, J=7.3 Hz), 6.64 (1H, t, J=7.2 Hz), 5.37 (1H, q, J=6.1 Hz), 4.97 (1H, br), 4.88 (1H, br), 4.64 (2H, br), 3.80 (3H, d, J=5.7 Hz), 3.72-3.67 (4H, m), 3.53-3.49 (2H, m), HRMS (ESI): m/z calcd for C$_{19}$H$_{21}$FN$_4$OS [M+H]$^+$ 373.1420. found.

Synthesis of Compound 8-13 (P2-7)

4-bromo crotonic acid, 2-bromo ethanoic acid or 3-bromo propanoic acid (0.097 mmol) was dissolved in anhydrous THF (1 mL) and basified with Et$_3$N (13.4 µL, 0.097 mmol). Then, iso-butyl chloroformate (IBCF: 12.1 µL, 0.097 mmol) was added slowly thereto at −15° C., followed by reaction for 15 minutes. Meanwhile, anhydrous THF (1 mL) with Compound 6a-d (0.107 mmol) and Et$_3$N (14.9 µL, 0.107 mmol) dissolved therein was added to the reaction solution prepared in advance, followed by reaction at 0° C. for 10 minutes and further reaction at room temperature for 2 hours. A mixed solution of water (1 mL) and anhydrous THF (0.5 mL) with 1-(2-fluoroethyl)piperazine (14.2 mg, 0.107 mmol) and Et$_3$N (44.8 µL, 0.322 mmol) dissolved therein was further added thereto, followed by reaction at room temperature for two hours. The reaction solution was mixed with a small amount of water and extracted with ethyl acetate. The organic layer was washed with saturated saline and dried with sodium sulfate. The solvent was evaporated to dryness, and the residue thus obtained was preparatively purified by reversed-phase HPLC.

(S,E)-4-(4-(2-Fluoroethyl)piperazin-1-yl)-1-(4-((2-hydroxy-1phenylethyl)amino)-5,8-dihydropyrido[4', 3':4,5]thieno[2,3-d]pyrimidin-7(6H)-yl)but-2-en-1-one (Compound 8: P2)

Compound 8 (P2) was synthesized using Compound 6a and 2-bromo crotonic acid. Yield 14.8 mg (11.2%), $^1$H NMR (500 MHz, DMSO-d$_6$) δ8.24 (1H, s), 7.42 (2H, d, J=7.7 Hz), 7.30 (2H, t, J=7.6 Hz), 7.22 (1H, t, J=7.3 Hz), 7.03-6.89 (1H, m), 6.73-6.66 (1H, m), 6.57-6.53 (1H, m), 5.34 (1H, s), 4.94-4.76 (3H, m), 4.66 (1H, m), 4.00-3.96 (2H, m), 3.83-3.69 (4H, m), 3.28-3.15 (12H, br), HRMS (ESI): m/z calcd for $C_{27}H_{33}FN_6O_2S$ [M+H]$^+$ 525.2370. found.

(S)-2-(4-(2-Fluoroethyl)piperazin-1-yl)-1-(4-((2-hydroxy-1phenylethyl)amino)-5,8-dihydropyrido[4',3':4,5]thieno[2,3-d]pyrimidin-7(6H)-yl)ethan-1-one (Compound 9: P3)

Compound 9 (P3) was synthesized using Compound 6a and 2-bromo ethanoic acid. Yield 13.0 mg (10.4%), $^1$H NMR (500 MHz, DMSO-$d_6$) δ8.24 (1H, s), 7.42 (2H, d, J=7.4 Hz), 7.33-7.29 (2H, m), 7.23 (1H, m), 6.56 (1H, dd, J=7.2 and 10 Hz), 5.34 (1H, m), 4.87-4.75 (4H, m), 4.66 (1H, br), 3.94-3.75 (4H, m), 3.53-3.17 (14H, br), HRMS (ESI): m/z calcd for $C_{25}H_{31}FN_6O_2S$ [M+H]$^+$ 499.2213. found.

(S)-3-(4-(2-Fluoroethyl)piperazin-1-yl)-1-(4-((2-hydroxy-1phenylethyl)amino)-5,8-dihydropyrido[4',3':4,5]thieno[2,3-d]pyrimidin-7(6H)-yl)propan-1-one (Compound 10: P4)

Compound 10 (P4) was synthesized using Compound 6a and 3-bromo propanoic acid. Yield 5.90 mg (4.60%), $^1$H NMR (500 MHz, DMSO-$d_6$) δ8.23 (1H, s), 7.42 (2H, d, J=7.4 Hz), 7.31 (2H, t, J=7.6 Hz), 7.23 (1H, m), 6.55 (1H, t, J=7.6 Hz), 5.34 (1H, m), 4.86-4.74 (3H, m), 4.68 (2H, br), 4.59 (2H, br), 4.47 (1H, br), 3.94-3.84 (6H, m), 3.57-3.51 (2H, m), 3.34 (3H, br), 3.19 (1H, br), 3.00 (2H, br), 2.92 (2H, br), HRMS (ESI): m/z calcd for $C_{26}H_{33}FN_6O_2S$ [M+H]$^+$ 513.2370. found.

(R,E)-4-(4-(2-Fluoroethyl)piperazin-1-yl)-1-(4-((1-phenylethyl)amino)-5,8-dihydropyrido[4',3':4,5]thieno[2,3-d]pyrimidin-7(6H)-yl)but-2-en-1-one (Compound 11: P5)

Compound 11 (P5) was synthesized using Compound 6b and 4-bromo crotonic acid. Yield 9.98 mg (18.3%), $^1$H NMR (400 MHz, DMSO-$d_6$) δ8.27 (1H, s), 7.45 (2H, d, J=7.2 Hz), 7.31 (2H, t, J=7.7 Hz), 7.23 (1H, br), 6.93 (1H, br), 6.69 (1H, br), 6.52 (1H, br), 5.45 (1H, q, J=7.1 Hz), 4.92-4.76 (3H, m), 4.64 (1H, br), 3.92 (2H, br), 3.65 (1H, br), 3.24-3.14 (12H, br), 1.56 (3H, d, J=7.0 Hz), HRMS (ESI): m/z calcd for $C_{27}H_{33}FN_6OS$ [M+H]$^+$ 509.2421. found.

(S,E)-4-(4-(2-Fluoroethyl)piperazin-1-yl)-1-(4-(2,2,2-trifluoro-1-phenylethoxy)-5,8-dihydropyrido[4',3':4,5]thieno[2,3-d]pyrimidin-7 (6H)-yl)but-2-en-1-one (Compound 12: P6)

Compound 12 (P6) was synthesized using Compound 6c and 4-bromo crotonic acid. Yield 14.0 mg (16.9%), $^1$H NMR (400 MHz, DMSO-$d_6$) δ8.59 (1H, s), 7.66 (2H, br), 7.46 (3H, br), 7.08 (1H, q, J=6.8 Hz), 6.86 (1H, br), 6.70 (1H, br), 5.01-4.83 (2H, m), 4.57 (1H, t, J=4.8 Hz), 4.45 (1H, t, J=4.8 Hz), 4.01 (1H, br), 3.80 (1H, br), 3.41-3.34 (11H, br), 3.15-3.10 (3H, br), HRMS (ESI): m/z calcd for $C_{27}H_{29}F_4N_5O_2S$ [M+H]$^+$ 564.1978 found.

(S,E)-4-(4-(2-Fluoroethyl)piperazin-1-yl)-1-(4-((2-methoxy-phenylethyl)amino)-5,8-dihydropyrido[4',3':4,5]thieno[2,3-d]pyrimidin-7(6H)-yl)but-2-en-1-one (Compound 13: P7)

Compound 13 (P7) was synthesized using Compound 6d and 4-bromo crotonic acid. Yield 7.57 mg (16.0%), $^1$H NMR (400 MHz, DMSO-$d_6$) δ8.30 (1H, s), 7.47 (2H, d, J=7.0 Hz), 7.33 (2H, t, J=7.4 Hz), 7.26 (1H, br), 6.90-6.82 (1H, m), 6.70 (1H, d, J=7.0 Hz), 6.27 (1H, d, J=16 Hz), 5.60 (1H, q, J=6.7 Hz), 4.94 (1H, br), 4.85 (1H, br), 4.76 (1H, br), 4.64 (3H, br), 4.16 (2H, d, J=5.8 Hz), 3.97 (1H, br), 3.87-3.82 (2H, m), 3.71-3.68 (3H, m), 3.55 (2H, br), 3.41-3.30 (9H, m), HRMS (ESI): m/z calcd for $C_{28}H_{35}FN_6O_2S$ [M+H]$^+$ 539.2526. found.

(Step C)

Synthesis of Compound 15 ([$^{18}$F]P1), Compound 18a ([$^{18}$F]P2) and Compound 18b ([$^{18}$F]P5)

Compounds 15, 18a and 18b([$^{18}$F]P1, 2, 5) were synthesized according to the following scheme 3.

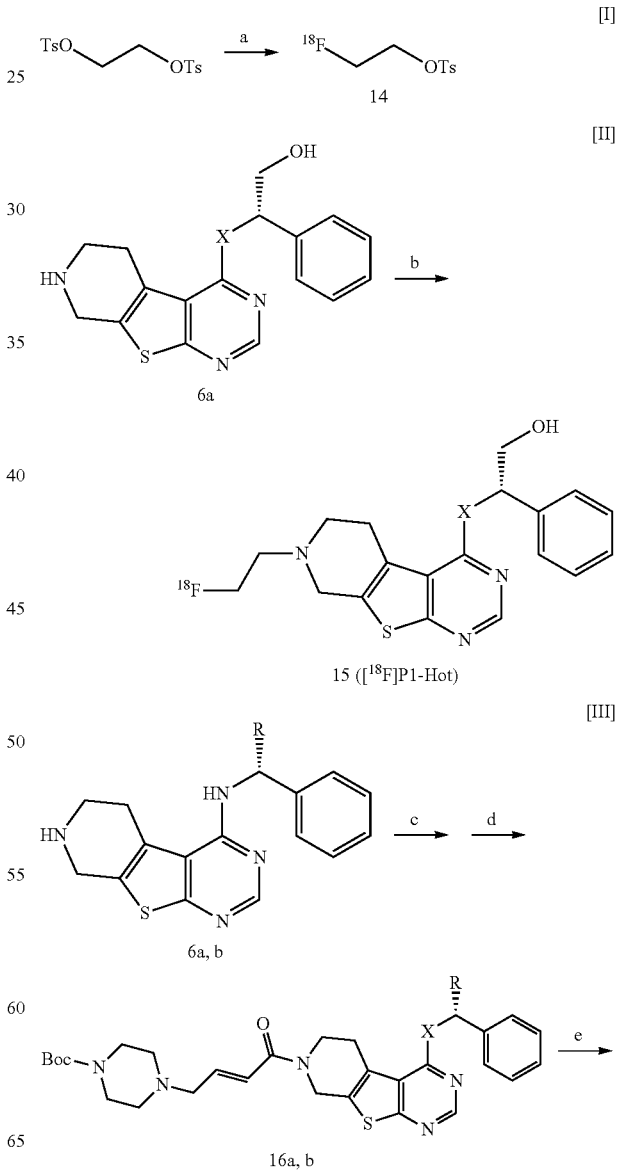

Scheme 3. Synthesis of compounds
[I] 2-[$^{18}$F]fluoroethyl-4-toluene sulfonate, [II] [$^{18}$F]Compound 1,
[III] [$^{18}$F]Compound 2 and [$^{18}$F]Compound 5 (Hot form).

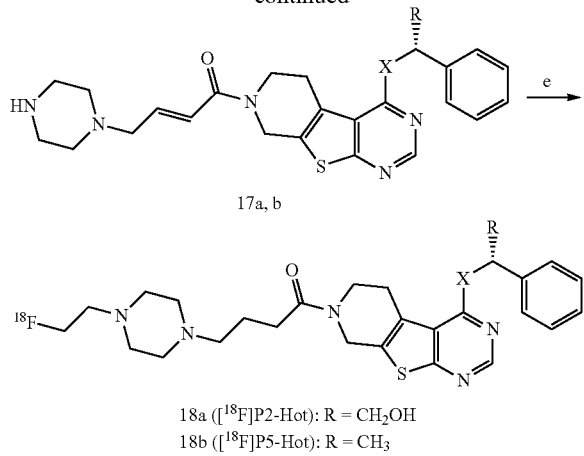

18a ([¹⁸F]P2-Hot): R = CH₂OH
18b ([¹⁸F]P5-Hot): R = CH₃

Reagents and conditions: (a) [¹⁸F]KF, Kryptofix2.2.2., K₂CO₃ in CH₃CN; (b) 14 in CH₃CN, 110° C., 20 min; (c) 4-bromo crotonic acid, IBCF, Et₃N in THF, -15° C→r.t.; (d) 1-(tert-butyloxycarbonyl)piperazine, Et₃N; (e) TFA; (f) 14 in DMF + CH₃CN, K₂CO₃, 110° C., 20 min.

Synthesis of Compounds 16a and 16b 4-bromo crotonic acid (8.58 mg, 0.052 mmol) was dissolved in anhydrous THF (1 mL) and basified with Et₃N (7.30 μL, 0.052 mmol). Then, IBCF (6.90 μL, 0.052 mmol) was slowly added thereto at −15° C., followed by reaction for 15 minutes. Meanwhile, anhydrous THF (1 mL) with Compound 6a or 6b (0.058 mmol) and Et₃N (8.10 μL, 0.058 mmol) dissolved therein was added to the reaction solution prepared in advance, followed by reaction at 0° C. for 10 minutes and further reaction at room temperature for two hours. A mixed solution of water (1 mL) and anhydrous THF (0.5 mL) with 1-(tert-butyloxycarbonyl)piperazine (9.77 mg, 0.052 mmol) and Et₃N (21.9 μL, 0.157 mmol) dissolved therein was further added thereto, followed by reaction for two hours. The reaction solution was mixed with a small amount of water and extracted with ethyl acetate. The organic layer was washed with saturated saline and dried with sodium sulfate. The solvent was evaporated to dryness, and the residue thus obtained was used in the next reaction without being purified.

tert-Butyl (S,E)-4-(4-(4-((2-hydroxy-1phenylethyl)amino)-5,8-dihydropyrido[4',3':4,5]thieno[2,3-d]pyrimidin-7 (6H)-yl)-4-oxobut-2-en-1-yl) piperazine-1-carboxylate (Compound 16a)

Compound 16a was prepared using Compound 6a as a material. Yield 25.3 mg (75.1%), LCMS (ESI): m/z 579.14 [M+H]⁺.

tert-Butyl (R,E)-4-(4-oxo-4-(4-((1-phenylethyl) amino)-5,8-dihydropyrido[4',3':4,5]thieno[2,3-d] pyrimidin-7(6H)-yl)but-2-en-1-yl)piperazine-1-carboxylate (Compound 16b)

Compound 16b was prepared using Compound 6b as a material. Yield 46.7 mg (72.5%), LCMS (ESI): m/z 563.30 [M+H]⁺.

General Synthesis of Compounds 17a and 17b

TFA (54.2 μL, 0.730 mmol) was added to Compound 16a or 16b (0.073 mmol) at 0° C., which then was reacted at room temperature for one hour. The reaction solution was mixed with water and extracted with ether. The water layer was collected and the solvent was evaporated to dryness, and then water and methanol were added to the residue to evaporate the solvent to dryness. This operation was repeated three times, and thereby TFA was removed. The residue thus obtained was sufficiently dried with a vacuum pump and used in the next reaction.

(S,E)-1-(4-((2-Hydroxy-1-phenylethyl)amino)-5,8-dihydropyrido[4',3':4,5]thieno[2,3-d]pyrimidin-7 (6H)-yl)-4-(piperazin-1-yl)but-2-en-1-one (Compound 17a)

Yield 24.5 mg (70.0%), LCMS (ESI): m/z 479.10 [M+H]⁺.

(R,E)-1-(4-((1-phenylethyl)amino)-5,8-dihydropyrido[4',3':4,5]thieno[2,3-d]pyrimidin-7(6H)-yl)-4-piperazin-1-yl)but-2-en-1-one (Compound 17b)

Yield 34.5 mg (90.0%), LCMS (ESI): m/z 463.20 [M+H]⁺.

[Radiochemical Synthesis]

Synthesis of 2-[¹⁸F]Fluoroethyl-4-toluene sulfonate (Compound 14)

Kryptofix 2.2.2. (4.50 mg) and acetonitrile (0.5 mL) were added to a [¹⁸F]fluoride solution (3700 MBq), which then was heated under N₂ stream at 120° C. to be azeotropically dehydrated. Acetonitrile was added thereto again and azeotropic dehydration was repeated. This was dissolved in anhydrous acetonitrile (0.25 mL) and ethylenglycol-1,2-ditosylate (6.75 nmol 2.50 mg) was added thereto, followed by reaction at 90° C. for five minutes. Water (0.12 mL) was added to the reaction solution, which then was preparatively purified by reversed-phase HPLC [COSMOSIL 5C18-AR-II, 10×250 mm, eluent 50% (A) and (B), flow rate 4.0 mL/min, λ=280 nm, Rt=10 to 11 min]. Water was added to the fraction of the target thus obtained to dilute it, which then was applied to Sep-Pak C18 Light Cartridge (Nihon Waters K.K.). Thereafter, water was run through it and thereby TFA was removed. The cartridge was dried under N2 stream and acetonitrile was run through it. Thus, the target was eluted.

Synthesis of radioactive labeled products 15, 18a and 18b ([¹⁸F]P1, 2 and 5)

For radioactive labeled products 18a and 18b, the precursor 17a or 17b (2.10 nmol) and K₂CO₃ (210 nmol, 29.0 mg) were dissolved in anhydrous DMF (60 μL), which then was added to an acetonitrile solution (90 μL) of Compound 14. Furthermore, Et₃N (10 μL) was added thereto, which then was reacted at 110° C. for 20 minutes. Only for a radioactive labeled product 15, the precursor 6a was reacted with an acetonitrile solution (150 μL) of Compound 14 under non-basicity. The reaction solution was dried under Ar stream, and the residue thus obtained was dissolved in a mixed solvent of water/acetonitrile (v/v=70/30, 0.15 mL) and preparatively purified by reversed-phase HPLC [COSMOSIL 5C₁₈-AR-II, 10×250 mm, gradient of 85:15 (0 min)→70:30 (5 min)→65:35 (15 min)→0:100 (20 min) by (A) and (B), flow rate 5.0 mL/min, λ=280 nm]. Water was added to the fraction of the target thus obtained to dilute it, which then was applied to Sep-Pak C18 Light Cartridge (Nihon Waters K.K.). Thereafter, water was run through it and thereby TFA was removed. The cartridge was dried under N₂ stream and acetonitrile was run through it. Thus, the target was eluted. Further, the solvent was evaporated to dryness and then it was dissolved in physiologic saline. This was used for the biological evaluation. The radiochemical yields of [$^{18}$F]P1, 2 and 5 were 5.4%, 3.6% and 2.1%, respectively, and the radiochemical purities thereof were all 99%.

[EGFR Tyrosine Kinase Inhibiting Activity Measurement]

The inhibiting activity of each Compound (P1 to P10) with respect to EGFR tyrosine kinase was measured using EGFR Kinase Enzyme Systems (Promega) and ADP-Glo™ Kinase assay Kit (Promega, Catalog No. V9101).

Four types of EGFR Kinase Enzyme Systems, specifically, EGFR Kinase Enzyme System (Catalog No. V3831), EGFR (L858R) Kinase Enzyme System (Catalog No. V5322), EGFR (T790M) Kinase Enzyme System (Catalog No. V4506), and EGFR (T790M, L858R) Kinase Enzyme System (Catalog No. V5324) were used (all of them were manufactured by Promega).

The measurement was carried out according to the Promega protocol applications guide. That is, a buffer solution (40 mM Tris-HCl, pH 7.5, 20 mM MgCl$_2$, 50 μM DTT and 0.1 mg/mL BSA) was used as a dilute solution. The concentration of each compound started at 20 μM (the final concentration, including 1% DMSO) with 5-fold dilutions with the buffer solution. Thus, ten concentrations of each compound were prepared. Then, 2 μL of each concentration of each compound thus obtained was added to each well of a 384-well plate. Furthermore, 4 μL (20 ng) of an EGFR Kinase Buffer that came with each EGFR Kinase Enzyme System was added to each well, which then was incubated at room temperature for ten minutes. Subsequently, 4 μL of mixed solution of ATP (10 μM) and Poly(Glu, Tyr) (2 μg) substrate was added to each well, which then was incubated at room temperature for one hour. Then, 10 μL of ADP-Glo™ Reagent (ADP-Glo™ Kinase Assay, Promega) was added to each well, which then was reacted at room temperature for 40 minutes. Furthermore, 20 μL of Kinase Detection Reagent (ADP-Glo™ Kinase Assay, Promega) was added to each well, which then was reacted at room temperature for one hour. Thereafter, the amount of luminescence was measured using Luminescence Counter 1420 ARVO™ Light (PerkinElmer Japan Co., Ltd.). From the data thus obtained, dose-response curves and IC$_{50}$ were calculated using GraphPad Prism 5 (GraphPad Software, Inc.). The results are shown in Table 1 below. In Table 1 below, WT indicates the measurement results obtained with the EGFR Kinase Enzyme System, L858R indicates the measurement results obtained with the EGFR (L858R) Kinase Enzyme System, T790M indicates the measurement results obtained with the EGFR (T790M) Kinase Enzyme System, and DM indicates the measurement results obtained with the EGFR (T790M, L858R) Kinase Enzyme System.

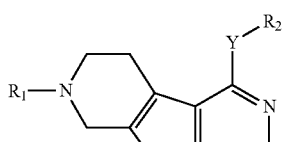

| R$_1$ |
| --- |
| P1 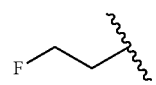 |
| P2 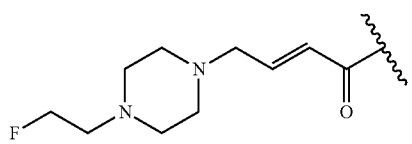 [SMILES: *C(=O)/C=C/CN1CCN(CCF)CC1] |
| P3 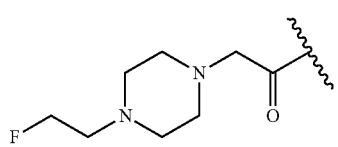 [SMILES: *C(=O)CN1CCN(CCF)CC1] |
| P4 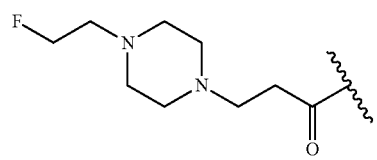 [SMILES: *C(=O)CCN1CCN(CCF)CC1] |
| P5 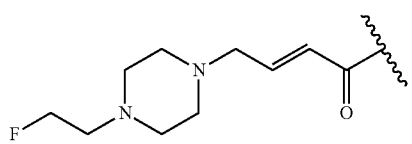 [SMILES: *C(=O)/C=C/CN1CCN(CCF)CC1] |

-continued
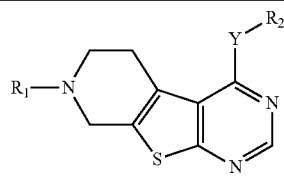
| | |
|---|---|
| P6 | 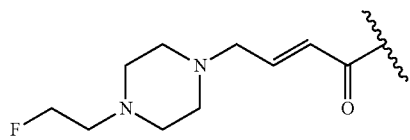 [SMILES: *C(=O)/C=C/CN1CCN(CCF)CC1] |
| P7 | 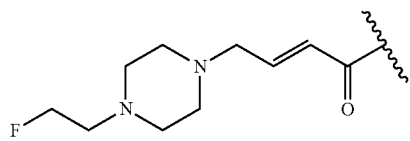 [SMILES: *C(=O)/C=C/CN1CCN(CCF)CC1] |
| P8 | 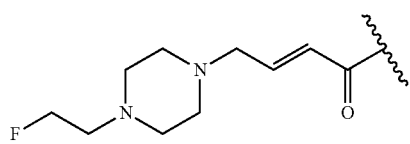 [SMILES: *C(=O)/C=C/CN1CCN(CCF)CC1] |
| P9 | 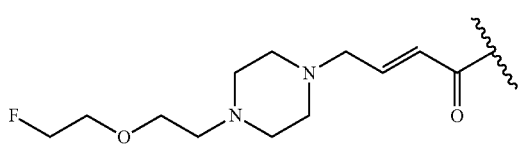 [SMILES: *C(=O)/C=C/CN1CCN(CCOCCF)CC1] |
| P10 | 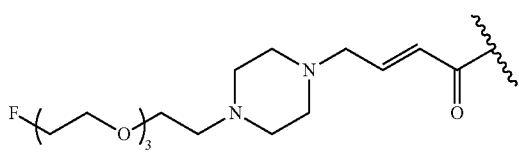 |
| Gefitinib | |
| | | | EGFR Kinase inhibition: IC$_{50}$ (μM) | | | |
|---|---|---|---|---|---|---|
| | Y | R$_2$ | WT | L858R | T790M | DM |
| P1 | HN⤳ | ⤳OH, phenyl | 2.309 | 3.414 | no active | no active |
| P2 | HN⤳ | ⤳OH, phenyl | 0.044 | 0.009 | 8.966 | >10 |
| P3 | HN⤳ | ⤳OH, phenyl | 4.370 | 2.674 | no active | no active |

-continued

| | R1 | Y-R2 | | | | |
|---|---|---|---|---|---|---|
| P4 | HN- | -OH, CH2Ph (S) | 2.827 | 1.835 | no active | no active |
| P5 | HN- | CH2Ph (wedge) | 0.130 | 0.027 | >10 | >10 |
| P6 | O- | CF3, CH2Ph | 0.896 | 0.336 | no active | >10 |
| P7 | HN- | OCH3, CH2Ph | 0.374 | 0.051 | no active | no active |
| P8 | HN- | 3-Br-phenyl | 4.308 | 1.383 | no active | no active |
| P9 | HN- | OH, Ph | 0.067 | 0.031 | >10 | >10 |
| P10 | HN- | OH, CH2Ph | 0.090 | 0.052 | >10 | >10 |
| Gefitinib | | | 0.020 | 0.021 | 0.868 | 7.111 |

>10: <50% enzyme inhibition at 10 μM.
no active: the activity is almost no at maximal concentration (20 μM) in this assay.

As shown in Table 1, P1 to P10 each showed a relatively high binding affinity to the L858R-mutated EGFR but showed no binding affinity to the L858R/T790M-mutated EGFR (DM in Table 1).

[Cellular Uptake Experiment]

H3255 cells ($4.0 \times 10^5$ cells/well), which are L858R mutant cells, were cultured in a 12-well plate for 24 hours. After the medium was removed, each well was washed with PBS(−) once. Each fetal bovine serum-free DMEM/Ham's F-12 medium with [$^{18}$F]P2 and gefitinib (0, 0.5, 1, and 2.5 μM) added thereto was added to each well, which then was incubated in a CO$_2$ incubator for two hours. Each well was washed with 0.1% Tween 80/1% DMSO/PBS(−) three times, and the cells were dissolved with 0.2 N NaOH. The radioactivity of each solution was measured with the gamma counter, and the protein concentration was determined using a BCA Protein Assay Kit (Pierce, Rockford, Ill.) and then the measurement results were analyzed. FIG. 1 shows the results.

As shown in FIG. 1, the uptake of [$^{18}$F]P2 into the H3255 cells was inhibited by gefitinib, which is EGFR-TKI.

[PET/CT Imaging]

(1) Imagining Using H3255 (L858R Mutant) Tumor-Bearing Mouse

[$^{18}$F]P2 (14.3 MBq/140 μL) was administered to a H3255 tumor-bearing mouse through a tail vein. He was anesthetized by inhalation of isoflurane (2.0%) from 175 minutes after the administration and then was imaged for 20 minutes from 180 minutes after the administration using a PET/CT device (FX-3300). Thereafter, CT imaging (60 kV, 320 μA) was carried out. The image reconstruction was carried out using 3D-OSEM. After imaging, the mouse was slaughtered and each organ was removed. Then, the mass and the radioactivity of each organ were measured, and the amount of accumulation (% ID/g) was calculated from the radioactivity per unit weight. As a result, the tumor/blood ratio was 3.23, the tumor/muscle ratio was 5.97, and the tumor/lung ratio was 2.66, and thereby high adjacent organ ratios were confirmed. Images acquired by the imaging are shown in FIG. 2A. In FIG. 2A, the circled portion is the portion with H3255 implanted thereto. As shown in FIG. 2A, it was confirmed that [$^{18}$F]P2 was accumulated specifically in the portion of the L858R-mutated EGFR, and thus [$^{18}$F]P2 allowed the L858R-mutated EGFR to be imaged.

<Imaging Conditions>
Animal: Balb/c nu/nu mouse, 8 w, male, 21.0 g
Cell: H3255 (1×10$^7$ cells/100 mL)
Injection Dose: 14.25 MBq/140 mL
PET/CT: FX-3300 (GMI)
Image Acquisition: 180 to 200 min after administration
Reconstruction: 3D-OSEM
Condition of CT: 60 kV, 320 mA (2) Imagining Using H1975 (L858R/T790M Mutant) Tumor-Bearing Mouse

[$^{18}$F]P2 (9.1 MBq/140 μL) was administered to a H1975 tumor-bearing mouse through a tail vein. He was anesthetized by inhalation of isoflurane (2.0%) from 175 minutes after the administration and then was imaged for 20 minutes from 180 minutes after the administration using a PET/CT device (FX-3300). Thereafter, CT imaging (60 kV, 320 μA) was carried out. The image reconstruction was carried out using 3D-OSEM. After imaging, the mouse was slaughtered and each organ was removed. Then, the mass and the radioactivity of each organ were measured, and the amount of accumulation (% ID/g) was calculated from the radioactivity per unit weight. As a result, the tumor/blood ratio was 1.29, the tumor/muscle ratio was 2.04, and the tumor/lung ratio was 0.98, and thereby it was confirmed that the adjacent organ ratios were significantly lower than those of the H3255 tumor-bearing mouse. Images acquired by the imaging are shown in FIG. 2B. In FIG. 2B, the circled portion is the portion with H1975 implanted thereto. As shown in FIG. 2B, it was confirmed that [$^{18}$F]P2 was not accumulated in the portion of the L858R/T790M-mutated EGFR.

<Imaging Conditions>
Animal: Balb/c nu/nu mouse, 8 w, male, 20.7 g
Cell: H1975 (5×10$^6$ cells/100 mL)
Injection Dose: 9.125 MBq/140 mL
PET/CT: FX-3300 (GMI)
Image Acquisition: 180 to 200 min after administration
Reconstruction: 3D-OSEM
Condition of CT: 60 kV, 320 mA The results of the PET/CT imaging described above showed that imaging using [$^{18}$F]P2 allows an EGFR gene in a cancer tissue (a tumor) to be determined to be L858R-mutated or L858R/T790M-mutated. Thus, the imaging allowed to determine whether a secondary mutation was developed or not and whether it had EGFR-TKI resistance or not.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A compound represented by Formula (1) or a pharmaceutically acceptable salt thereof:

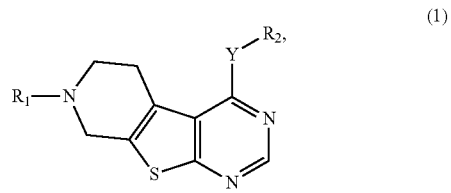

(1)

wherein R$_1$ is a group represented by Formula (a), (b) or (c):

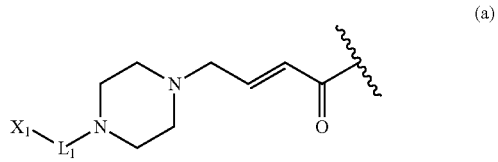

(a)

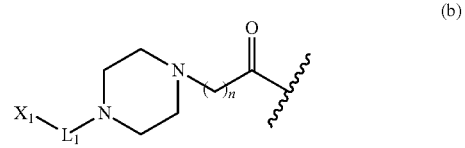

(b)

(c)

$R_2$ is a group represented by Formula (d) or (e):

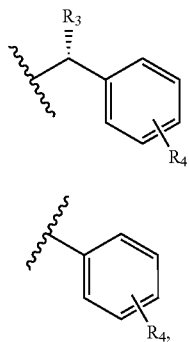
(d)

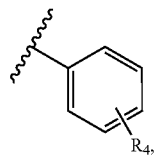
(e)

and

Y is —NH— or —O—, wherein in Formulae (a) and (b), $L_1$ is, an alkanediyl group having 1 to 10 carbon atoms, or

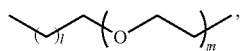

wherein l is 0 to 5, and m is 1 to 5, in Formulae (b) and (c), n is an integer of 1 to 3, in Formulae (a), (b) and (c), $X_1$ is a radioactive halogen atom, in Formula (d), $R_3$ is an alkyl group having 1 to 4 carbon atoms substituted with halogen, a hydroxyalkyl group having 1 to 4 carbon atoms, or an alkoxyalkyl group having 1 to 4 carbon atoms, and in Formulae (d) and (e), $R_4$ is a hydrogen atom or a halogen atom.

2. The compound according to claim 1, wherein $L_1$ is an ethanediyl group, an ethyleneoxyethylene group, or an ethylenetrioxyethylene group.

3. The compound according to claim 1, wherein $R_3$ is a trifluoromethyl group, a hydroxymethyl group, or a methoxymethyl group.

4. The compound according to claim 1, wherein $R_4$ is a hydrogen atom or a bromine atom.

5. A nuclear medicine diagnostic imaging agent, comprising a compound according to claim 1.

6. The compound according to claim 1, wherein $R_1$ is a group represented by Formula (a).

7. A compound represented by Formula (1) or a pharmaceutically acceptable salt thereof:

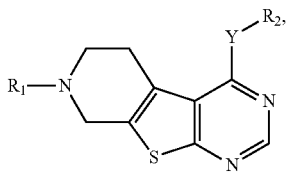
(1)

wherein $R_1$ is a group represented by Formula (a), (b) or (c):

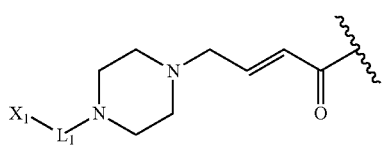
(a)

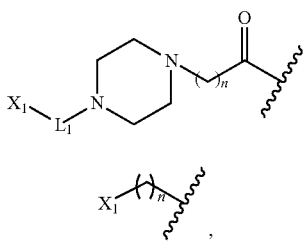
(b)

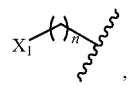
(c)

$R_2$ is a group represented by Formula (d)

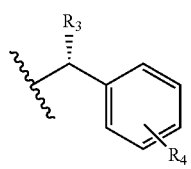
(d)

Y is —NH— or —O—, wherein in Formulae (a) and (b), $L_1$ is a bond, an alkanediyl group having 1 to 10 carbon atoms, or

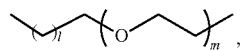

wherein l is 0 to 5, and m is 1 to 5, in Formulae (b) and (c), n is an integer of 1 to 3, in Formulae (a), (b) and (c), $X_1$ is a radioactive halogen atom, in Formula (d), $R_3$ is an alkyl group having 1 to 4 carbon atoms substituted with halogen, a hydroxyalkyl group having 1 to 4 carbon atoms, or an alkoxyalkyl group having 1 to 4 carbon atoms, and $R_4$ is a hydrogen atom or a halogen atom.

8. A compound represented by Formula (3) or a pharmaceutically acceptable salt thereof:

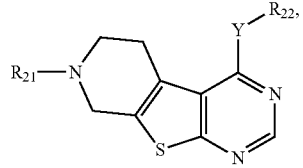
(3)

wherein $R_{21}$ is a group represented by Formula (j), (k) or (l):

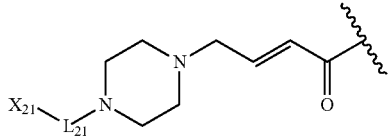
(j)

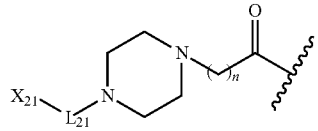
(k)

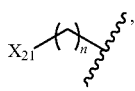 (l)

$R_{22}$ is a group represented by Formula (m):

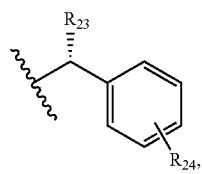 (m)

and
Y is —NH— or —O—,
wherein in Formulae (j) and (k), $L_{21}$ is a bond, an alkanediyl group having 1 to 10 carbon atoms, or

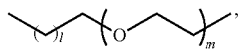

wherein l is 0 to 5, and m is 1 to 5,
in Formulae (k) and (I), n is an integer of 1 to 3,
in Formulae (j), (k) and (I), $X_{21}$ is a halogen atom,
in Formula (m), $R_{23}$ is an alkyl group having 1 to 4 carbon atoms substituted with halogen, a hydroxyalkyl group having 1 to 4 carbon atoms, or an alkoxyalkyl group having 1 to 4 carbon atoms, and $R_{24}$ is a hydrogen atom or a halogen atom.

9. The compound according to claim 8, wherein $R_{23}$ is a trifluoromethyl group, a hydroxymethyl group, or methoxymethyl group.

10. The compound according to claim 8, wherein $R_{21}$ is a group represented by Formula (j).

11. The compound according to claim 8, wherein $R_{21}$ is a group represented by Formula (k).

12. The compound according to claim 8, wherein $R_{21}$ is a group represented by Formula (I).

\* \* \* \* \*